(12) United States Patent
Santerre et al.

(10) Patent No.: US 8,696,750 B2
(45) Date of Patent: Apr. 15, 2014

(54) FIBROUS SCAFFOLD FOR USE IN SOFT TISSUE ENGINEERING

(75) Inventors: J. Paul Santerre, Whitby (CA); Rita Kandel, Toronto (CA)

(73) Assignee: Mount Sinai Hospital (CA)

( * ) Notice: Subject to any disclaimer, the term of this patent is extended or adjusted under 35 U.S.C. 154(b) by 925 days.

(21) Appl. No.: 12/526,790

(22) PCT Filed: Feb. 14, 2008

(86) PCT No.: PCT/CA2008/000291
§ 371 (c)(1),
(2), (4) Date: Feb. 25, 2010

(87) PCT Pub. No.: WO2008/098366
PCT Pub. Date: Aug. 21, 2008

(65) Prior Publication Data
US 2010/0234955 A1 Sep. 16, 2010

Related U.S. Application Data

(60) Provisional application No. 60/901,252, filed on Feb. 14, 2007.

(51) Int. Cl.
*A61F 2/44* (2006.01)
(52) U.S. Cl.
USPC ..................... 623/17.16; 623/17.11
(58) Field of Classification Search
None
See application file for complete search history.

(56) References Cited

U.S. PATENT DOCUMENTS

| | | | | |
|---|---|---|---|---|
| 4,579,899 A | * | 4/1986 | Kondo | 524/198 |
| 4,675,361 A | * | 6/1987 | Ward, Jr. | 525/92 A |
| 5,518,764 A | * | 5/1996 | Traubel et al. | 427/209 |
| 5,665,831 A | * | 9/1997 | Neuenschwander et al. | 525/415 |
| 5,741,872 A | * | 4/1998 | Smith | 526/301 |
| 6,770,725 B2 | | 8/2004 | Santerre et al. | |
| 7,413,575 B2 | * | 8/2008 | Phaneuf et al. | 623/1.54 |
| 7,494,614 B2 | | 2/2009 | Pilliar et al. | |
| 7,514,139 B2 | | 4/2009 | Ishida et al. | |
| 8,241,651 B2 | * | 8/2012 | Lahann | 424/422 |
| 2002/0072584 A1 | * | 6/2002 | Brady et al. | 528/480 |
| 2002/0111695 A1 | | 8/2002 | Kandel et al. | |
| 2004/0083001 A1 | | 4/2004 | Kandel et al. | |
| 2004/0197367 A1 | * | 10/2004 | Rezania et al. | 424/422 |
| 2005/0255079 A1 | | 11/2005 | Santerre et al. | |
| 2005/0255082 A1 | | 11/2005 | Santerre et al. | |
| 2006/0051394 A1 | * | 3/2006 | Moore et al. | 424/423 |
| 2006/0085063 A1 | * | 4/2006 | Shastri et al. | 623/1.41 |

(Continued)

FOREIGN PATENT DOCUMENTS

WO WO-07/098234 8/2007

OTHER PUBLICATIONS

Humphreys, "Neuroimaging in Low Back Pain", American Family Physician, 65(11):2299-2306 (Jun. 1, 2002).

(Continued)

*Primary Examiner* — Nicholas Woodall
(74) *Attorney, Agent, or Firm* — Howson & Howson LLP

(57) ABSTRACT

The present invention relates to a fibrous scaffold for use as a substrate in soft tissue applications, in particular for preparing annulus fibrosus (AF) tissue. In aspects, the present invention also relates to an engineered biological material comprising AF tissue; constructs comprising one or more engineered biological materials; methods for producing the biological materials and constructs; and methods of using the biological materials and constructs.

30 Claims, 14 Drawing Sheets

(56) References Cited

U.S. PATENT DOCUMENTS

| | | | |
|---|---|---|---|
| 2006/0182922 A1 | 8/2006 | Ishida et al. | |
| 2007/0037891 A1 | 2/2007 | Esfand et al. | |
| 2007/0071733 A1 | 3/2007 | Kandel et al. | |
| 2008/0119936 A1 | 5/2008 | Kandel et al. | |

OTHER PUBLICATIONS

Stevens, "CD44 Expression in the Developing and Growing Rat Intervertebral Disc", Developmental Dynamics, 219(3):381-390 (Nov. 2000).
Zhu, "The Role of the Hyaluronan Receptor CD44 in Mesenchymal Stem Cell Migration in the Extracellular Matrix", Stem Cells, 24(4):928-935 (Apr. 2006; Epub: Nov. 23, 2005).
Preliminary Amendment in U.S. Appl. No. 11/858,716 (Feb. 4, 2008).
Office Action Issued in U.S. Appl. No. 11/404,290 (Oct. 19, 2009).
Office Action Issued in U.S. Appl. No. 11/404,290 and Response thereto (Mar. 9, 2009).
Office Action Issued in U.S. Appl. No. 11/404,290 and Response thereto (Jun. 6, 2008).
Office Action Issued in U.S. Appl. No. 11/129,358 and Response thereto (Mar. 13, 2009).
Office Action Issued in U.S. Appl. No. 11/129,358 and Response thereto (Jan. 15, 2009).
Office Action Issued in U.S. Appl. No. 10/875,550 (Aug. 6, 2009).
Office Action Issued in U.S Appl. No. 10/875,550 and Response thereto (Feb. 13, 2009).
Office Action Issued in U.S. Appl. No. 10/875,550 and Response thereto (Jun. 24, 2008).
Office Action Issued in U.S. Appl. No. 10/875,550 and Response thereto (Mar. 27, 2008).
Preliminary Amendment in U.S. Appl. No. 10/875,550 (Oct. 5, 2004).
Alini, "The Potential and Limitations of a Cell-Seeded Collagen/Hyaluronan Scaffold to Engineer an Intervertebral Disc-Like Matrix", Spine (Phila PA 1976) 28(5):446-454 Discussion 453 (Mar. 1, 2003).
Anderson, "Intervertebral Disc Arthroplasty", Spine, 29(23):2779-2786 (Dec. 1, 2004).
Antonacci, "A Histologic Study of Fractured Human Vertebral Bodies", Journal of Spinal Disorders and Techniques, 15(2):118-126 (Apr. 2002).
Atta, "Compressive Properties and Curing Behaviour of Unsaturated Polyester Resins in the Presence of Vinyl Ester Resins Derived From Recycled Poly(Ethylene Terephthalate)", Journal of Polymer Research, 12(5):373-383 (Oct. 2005).
Battié, "Lumbar Disc Degeneration: Epidemiology and Genetics", Journal of Bone and Joint Surgery, 88(4):Supplemental 2:3-9 (Apr. 1, 2006).
Bogduk, "The Inter-Body Joints and the Intervertebral Discs Clinical Anatomy of the Lumbar Spine and Sacrum", New York: Churchill Livingstone, 13-31 (Jan. 15, 1997).
Chang, "Porous silk scaffolds can be used for tissue engineering annulus fibrosus", European Spine Journal, 16(11):1848-1857 (Nov. 2007; Epub: Apr. 20, 2007).
Choee, "Proliferation Rate of Fibroblast Cells on Polyethylene Surfaces With Wettability Gradient", Journal of Applied Polymer Science, 92(1):599-606 (Apr. 5, 2004).
Ernsting, "Generation of Cell Adhesion Substrates Using Peptide Fluoroalkyl Surface Modifiers", Biomaterials, 26(33):6536-6546 (Nov. 2005).
Fang, "Kinetics of Protein Adsorption and Desorption on Surfaces With Grafted Polymers", Biophysical Journal, 89(3):1516-1533 (Sep. 2005; Epub: Jul. 1, 2005).
Ferguson, "Biomechanics of the Aging Spine", European Spine Journal, 12 (Supplemental 2):S97-S103 (Oct. 2003; Epub: Sep. 9, 2003).
Gao, "Surface Hydrolysis of Poly(Glycolic Acid) Meshes Increases the Seeding Density of Vascular Smooth Muscle Cells", Journal of Biomedical Materials Research, 42(3):417-424 (Dec. 5, 1998).
Grunhagen, "Nutrient Supply and Intervertebral Disc Metabolism", The Journal of Bone and Joint Surgery, 88(Supplemental 2):30-35 (Apr. 2006).
Guan, "Functionalizing of Polyurethane Surfaces by Photografting With Hydrophilic Monomers" Journal of Applied Polymer Science, 77(11):2505-2512 (Sep. 12, 2000).
Gunatillake, "Biodegradable synthetic polymers for tissue engineering", European Cell Materials, 5:1-16 Discussion 16 (May 20, 2003).
Hallab, "Evaluation of Metallic and Polymeric Biomaterial Surface Energy and Surface Roughness Characteristics for Directed Cell Adhesion", Tissue Engineering, 7(1):55-71 (Feb. 2001).
Hamilton, "Formation of a Nucleus Pulposus-Cartilage Endplate Construct In Vitro", Biomaterials, 27(3):397-405 (Jan. 2006; Epub: Sep. 2, 2005).
Hayes, "Extracellular Matrix in Development of the Intervertebral Disc", Matrix Biology:Journal of the International Society for Matrix Biology, 20(2):107-121 (Apr. 2001).
Hayman, "Vitronectin—a Major Cell Attachment—Promoting Protein in Fetal Bovine Serum", Experimental Cell Research, 160(2):245-258 (Oct. 1985).
Ishihara, "Effects of Low Oxygen Concentrations and Metabolic Inhibitors on Proteoglycan and Protein Synthesis Rates in the Intervertebral Disc", Journal of Orthopaedic research : official publication of the Orthopaedic Research Society, 17(6):829-835 (Nov. 1999).
Kogerman, "CD44 protein levels and its biological activity are regulated in Balb/c 3T3 fibroblasts by serum factors and by transformation with the ras but not with the sis oncogene", Journal Cell Physiology, 169(2):341-349 (Nov. 1996).
Lee, "Development of a prosthetic intervertebral disc", Spine (Phila PA 1976), 16(6 Supplemental):S253-255 (Jun. 1991).
Li, "Ph-Compensation Effect of Bioactive Inorganic Fillers on the Degradation of PLGA", Composites Science and Technology, 65(14):2226-2232 (Nov. 2005).
Lin, "Surface Modification of Poly(L-Lactic Acid) to Improve Its Cytocompatibility Via Assembly of Poly Electrolytes and Gelatin", Acta Biomaterialia 2(2):155-164 (Mar. 2006; Epub: Dec. 7, 2005).
Lopez-Espina, "Multilevel Cervical Fusion and Its Effect on Disc Degeneration and Osteophyte Formation", Spine, 31(9):972-978 (Apr. 20, 2006)
Lotz, "Disc Regeneration: Why, When, and How", Neurosurgery Clinics of North America, 16(4):657-663 Vii. Review (Oct. 2005).
McKenzie, "Decreased functions of astrocytes on carbon nanofiber materials", Biomaterials 25(7-8):1309-1317 (Mar.-Apr. 2004).
Meinel, "Engineering Cartilage-Like Tissue Using Human Mesenchymal Stem Cells and Silk Protein Scaffolds", Biotechnology and Bioengineering, 88(3):379-391 (Nov. 5, 2004).
Merkesdal, "Prediction of Costs-Of-Illness in Patients With Low Back Pain Undergoing Orthopedic Outpatient Rehabilitation", International Journal of Rehabilitation Research, 28(2):119-126 (Jun. 2005).
Michiardi, "The Influence of Surface Energy on Competitive Protein Adsorption on Oxidized Niti Surfaces", Biomaterials, 28(4):586-594 (Feb. 2007).
Miller, "Lumbar Disc Degeneration: Correlation With Age, Sex, and Spine Level in 600 Autopsy Specimens", Spine, 13(2):173-178 (Feb. 1988).
Mizuno, "Tissue-Engineered Composites of Annulus Fibrosus and Nucleus Pulposus for Intervertebral Disc Replacement", Spine, 29(12):1290-1298 (Jun. 15, 2004).
Mizuno, "Biomechanical and biochemical characterization of composite tissue-engineered intervertebral discs", Biomaterials 27(3):362-370 (Jan. 2006; Epub: Sep. 13, 2005).
Nerurkar, "Mechanics of Oriented Electrospun Nanofibrous Scaffolds for Annulus Fibrosus Tissue Engineering", Journal of Orthopedic Research, 25(8):1018-1028 (Aug. 2007).
Redey, "Behavior of Human Osteoblastic Cells on Stoichiometric Hydroxyapatite and Type A Carbonate Apatite: Role of Surface Energy", Journal of Biomedical Materials Research, 50(3):353-364 (Jun. 5, 2000).
Riboldi, "Electrospun Degradable Polyesterurethane Membranes: Potential Scaffolds for Skeletal Muscle Tissue Engineering", Biomaterials, 26(22):4606-4615 (Aug. 2005).

(56) References Cited

OTHER PUBLICATIONS

Rong, "Proteoglycans Synthesized by Canine Intervertebral Disc Cells Grown in A Type I Collagen-Glycosaminoglycan Matrix", Tissue Engineering, 8(6):1037-1047 (Dec. 2002).
Sanders, "Fibro-porous meshes made from polyurethane micro-fibers: effects of surface charge on tissue response", Biomaterials 26(7):813-818 (Mar. 2005).
Sato, "An Atelocollagen Honey-Comb-Shaped Scaffold With a Membrane Seal (ACHMS-Scaffold) for the Culture of Annulus Fibrosus Cells From an Intervertebral Disc", Journal of Biomedical Materials Research, 64A(2):248-256 (Feb. 1, 2003).
Satriano, "Surface Free Energy and Cell Attachment Onto Ion-Beam Irradiated Polymer Surfaces", Nuclear Instruments and Methods in Physics Research Section B: Beam Interactions with Materials and Atoms, 208:287-293 (Aug. 2003).
Schneider, "The Effect of Hydrogel Charge Density on Cell Attachment", Biomaterials, 25(15):3023-3028 (Jul. 2004).
Shim, "CHARITE Versus Prodisc: A Comparative Study of a Minimum 3-Year Follow-Up", Spine, 32(9):1012-1018 (Apr. 20, 2007).
Choi, "Plasma-Induced Graft Co-Polymerization of Acrylic Acid Onto the Polyurethane Surface", Surface and Coatings Technology, 182(1):55-64 (Apr. 1, 2004).
Stankus, "Fabrication of Biodegradable Elastomeric Scaffolds With Sub-Micron Morphologies", Journal of biomedical Materials Research, 70(4):603-614 (Sep. 15, 2004).
Stankus, "Microintegrating Smooth Muscle Cells Into a Biodegradable, Elastomeric Fiber Matrix", Biomaterials, 27(5):735-744 (Feb. 2006; Epub: Aug. 10, 2005).
Tang, "Enzyme-Induced Biodegradation of Polycarbonate Polyurethanes: Dependence on Hard-Segment Concentration", Journal of Biomedical Materials Research, 56(4):516-528 (Sep. 15, 2001).
Thapa, "Nano-Structured Polymers Enhance Bladder Smooth Muscle Cell Function", Biomaterials, 24(17):2915-2926 (Aug. 2003).
Thonar, "Compartmentalization of the Matrix Formed by Nucleus Pulposus and Annulus Fibrosus Cells in Alginate Gel", Biochemical Society Transactions, 30(Part 6):874-878 (Nov. 2002).
Waldman, "Characterization of Cartilaginous Tissue Formed on Calcium Polyphosphate Substrates In Vitro", Journal of Biomedical Materials Research, 62(3):323-330 (Dec. 5, 2002).
Wilda, "In Vitro Studies of Annulus Fibrosus Disc Cell Attachment, Differentiation and Matrix Production on PDLLA/45S5 Bioglasss Composite Films", Biomaterials, 27(30):5220-5229 (Oct. 2006; Epub: Jun. 30, 2006).
Helen, "Three-Dimensional Culture of Annulus Fibrosus Cells Within PDLLA/Bioglass<(R)> Composite Foam Scaffolds: Assessment of Cell Attachment, Proliferation and Extrcellular Matrix Production", Biomaterials, 28(11):2010-2020 (Apr. 2007).
Woessner, "The Determination of Hydroxy Proline in Tissue and Protein Samples Containing Small Proportions of This Imino Acid", Archives of Biochemistry and Biophysics, 93:440-447 (May 1961).
Woo, "Synthesis and characterization of a novel biodegradable antimicrobial polymer", Biomaterials, 21; 1235-1246 (2000).
Yamamoto, "Quantitative Evaluation of Cell Attachment to Glass, Polystyrene, and Fibronectin- or Collagen-Coated Polystyrene by Measurement of Cell Adhesive Shear Force and Cell Detachment Energy", Journal of Biomedical Materials Research, 50(2):114-124 (May 2000).
Yang, "An In-Vitro Study on Regeneration of Human Nucleus Pulposus by Using Gelatin/Chondroitin-6-Sulfate/Hyaluronan Tri-Copolymer Scaffold", Artificial Organs, 29(10):806-814 (Oct. 2005).
Yang, "Gelatin/Chondroitin-6-Sulfate Copolymer Scaffold for Culturing Human Nucleus Pulposus Cells In Vitro With Production of Extracellular Matrix", Journal of Biomedical Materials Research, 74(1):488-494 (Jul. 2005).
Yang, "Synthesis and Characterization of a Novel Polymer-Ceramic System for Biodegradable Composite Application", Journal of Biomedical Materials Research, 66(3):622-632 (Sep. 1, 2003).
Yang, "Polar surface chemistry of nanofibrous polyurethane scaffold affects annulus fibrosus cell attachment and early matrix accumulation", Journal of Biomedical Materials Research, (Dec. 23, 2008 [Epub ahead of print]).
Yoganandan, "Intravertebral Pressure Changes Caused by Spinal Microtrauma", Neurosurgery, 35(3):415-421 Discussion 421 (Sep. 1994).
Zhong, "Formation of Collagen-Glycosaminoglycan Blended Nanofibrous Scaffolds and Their Biological Properties", Biomacromolecules, 6(6):2998-3004 (Nov.-Dec. 2005).
Zigler, "Results of the Prospective, Randomized, Multicenter Food and Drug Administration Investigational Devide Exemption Study of the Prodisc-L Total Disc Replacement Versus Circumferential Fusion for the Treatment of 1 -Level Degenerative Disc Disease", Spine, 32(11):1155-1162 Discussion 1163 (May 15, 2007).
International Preliminary Report on Patentability (including Written Opinion) in PCT/CA2008/000291—Issued Aug. 19, 2009.
Office Action (Final) Issued on U.S. Appl. No. 11/129,358 (Dec. 3, 2009).
Response to Office Action Aug. 6, 2009, Office Action in U.S. Appl. No. 10/875,550 (Feb. 5, 2010).

\* cited by examiner

A

B

A

B

C

A

B

A

B

A

B ered parallel to each other and about 65° C. from the vertical. Although the angle is the same, the direction of the inclination alternates with each sheet such that the fibres in one lamella are 65° to the right, while in the next lamella they are 65° to the left. Every second lamella has the same orientation. This very specific collagen organization allows the disc to rotate and flex. Collagen makes up about 70% of the dry weight of the annulus. Type I collagen is the predominant collagen but types II, III, V, VI and type IX collagen are also present in lesser amounts.

FIBROUS SCAFFOLD FOR USE IN SOFT TISSUE ENGINEERING

CROSS-REFERENCE TO RELATED APPLICATIONS

This application is a national stage of International Patent Application No. PCT/CA2008/000291, filed Feb. 14, 2008, which claims the benefit of the priority of U.S. Provisional Patent Application No. 60/901,252, filed Feb. 14, 2007 (expired), which applications are incorporated herein by reference.

FIELD OF THE INVENTION

The present invention relates to a fibrous scaffold for use in soft tissue applications, in particular for preparing annulus fibrosus (AF) tissue. The present invention also relates to an engineered biological material comprising soft tissue; constructs comprising one or more engineered biological materials; methods for producing the engineered biological materials and constructs; and methods of using the engineered biological materials or constructs.

BACKGROUND OF THE INVENTION

In an autopsy study, 97% of individuals 50 years or older had intervertebral disc degeneration, a disease process that involves both the annulus fibrosus and nucleus pulposus [1]. The etiology of this process is unknown but may be due to the relative avascularity of the tissue [2], calcification of the cartilage endplate [3], mechanical factors [4], vertebral body microfractures [5], loss of notochordal cells and/or genetic factors [6]. The low back pain that can develop in association with this disease is one of the most common afflictions in today's society and approximately eighty percent of people will experience at least one episode of low back pain at some time in their lives [7]. The direct costs of diagnosing and treating low back pain in the United States, as estimated by the American Chiropractic Association, is approximately $25 billion annually [8]. There is no optimal treatment for chronic back pain currently. Although there are several surgical options these all have limitations. Spinal fusion of diseased disc tissue may relieve pain faster, but it can result in reduced flexibility and the potential to develop degenerative changes in adjacent segments [9]. The intervertebral disc can be replaced with a synthetic prosthesis but this treatment is only appropriate for selected individuals [10, 11] and they can loosen over time [12]. Discectomy does not restore disc height and thus does not treat the underlying disease process. Therefore, there is a great interest in developing alternative biological treatments for this disease. One of the options is to tissue engineer a functional intervertebral disc that could be used to replace the degenerated disc [13].

The human spine consists of 33 vertebral bodies each separated, with the exception of C1 and C2 and the coccyx, by an intervertebral disc (IVD). The IVD anchors adjacent vertebral bodies and by doing so allows for spinal stabilization, load bearing, and movement. The intervertebral disc is a specialized structure consisting of three components, a gel-like nucleus pulposus (NP) which is surrounded by annulus fibrosus (AF), which are sandwiched between cartilage end plates (CEP) and vertebral bodies [14]. The normal function of the disc is dependent on maintenance of the composition, organization, and integrity of the different components.

The annulus fibrosus (FIG. 3) is the most complex of these 3 tissues present in the disc. It consists of approximately 10-20 lamellar sheets each composed of collagen fibres ori- To date, many studies have focused on the regeneration of NP [15-17] rather than AF tissue, probably because of the structural complexity of the AF tissue [18]. Even though AF tissue engineering has been attempted using various polymeric scaffolds including PDLLA/45S5 Bioglass® composite films [19], atelocollagen honeycomb [20], collagen—GAG [21], collagen—hyaluronan [22], polyglycolic acid/polylactic acid [23], and alginate [24] materials, in all of these scaffolds AF tissue formation has been limited and none has recapitulated the complex structure of the AF. Furthermore some scaffolds may not be optimal for this use. For example when polylactides, polyglycolides, and their copolymers degrade, they form acidic degradation products that can decrease the local pH, and overwhelm the tissue buffering and cell regulating capacities, which adversely affect biocompatibility [25]. Furthermore an acidic environment in the disc has been shown to greatly inhibit the rates of extracellular matrix synthesis [26], which may actually affect tissue formation. For these reasons there has been an interest in developing new polymers.

SUMMARY OF THE INVENTION

The present invention relates to a fibrous scaffold for use as a substrate in soft tissue applications or for culturing soft tissues, in particular for preparing AF tissue. In aspects of the invention the fibrous scaffold is a nanofiber porous scaffold comprising polyurethane polymers optionally with components that increase surface energy of the scaffold. In particular aspects the fibrous scaffold is a nanofiber porous scaffold comprising a polyurethane formulation comprising a polyurethane base polymer and novel anionic dihydroxyl oligomers (ADO).

In aspects of the invention, a polyurethane formulation is provided comprising a blend of polyurethane polymers and selected oligomers that increase surface energy in a scaffold or substrate formed from the formulation. In aspects of the invention, a polyurethane formulation is provided comprising fibres comprising a blend of polycarbonate urethane polymers and selected oligomers that increase surface energy in a scaffold or substrate formed from the formulation. In particular aspects of the invention, the fibres are random. In other particular aspects of the invention, the fibres are aligned.

In aspects of the invention, the selected oligomers are novel anionic dihydroxyl oligomers (ADO). Thus, the invention provides novel anionic dihydroxyl oligomers having one or more of the following properties:

a) about 50% to about 70%, about 50% to 60% or about 55% to 65% of its side chains comprise carboxylic acid groups;

b) absorption bands in the about 600 $cm^{-1}$ to about 4000 $cm^{-1}$ region by Fourier transform infrared spectroscopy (FTIR); and c) a peak corresponding to a urethane group at about 1680-1750 $cm^{-1}$, in particular 1720 to 1740 $cm^{-1}$, by FTIR.

The invention also relates to a process for producing the novel anionic dihydroxyl oligomer comprising linking a polyether diol with a carboxylic ester in the presence of a polyisocyanate to produce an oligomeric product, and hydrolzying the oligomeric product to produce the anionic dihydroxyl oligomer. The invention also contemplates an anionic dihydroxyl oligomer produced by a method of the invention.

The invention further relates to a fibrous scaffold or substrate produced or fabricated from a polyurethane formulation described herein, and a process for producing a fibrous scaffold of the invention.

In an aspect, the invention provides a fibrous scaffold for culturing soft tissues on its surface said scaffold comprising fibres comprising a blend of polyurethane polymers and oligomers wherein the oligomers increase surface energy of the scaffold and comprise polar groups that are exposed on the surface of the fibrous scaffold. In a particular aspect, the invention provides a fibrous scaffold for culturing soft tissues on its surface comprising fibres comprising a blend of polycarbonate urethane polymers and anionic dihydroxyl oligomers, wherein the fibres are aligned or random.

The invention provides an engineered biological material comprising in combination a fibrous scaffold of the invention and a soft tissue, in particular intervertebral disc tissue or a portion thereof, more particularly annulus fibrosus (AF) tissue. Further, the invention provides tissues derived from the biological material, and a process for producing the engineered biological material. Still further, the invention provides a construct comprising an engineered biological material of the invention or tissue therefrom.

In an aspect the invention provides an engineered biological material comprising or enriched for annulus fibrosus (AF) tissue. In particular, the invention relates to an engineered biological material comprising a continuous layer of annulus fibrosus (AF) tissue. The tissue formed in vitro mimics the organization of AF tissue in vivo. In particular, the collagen content of the AF tissue is or will be substantially the same as native AF tissue following implantation. The collagen content of the in vitro-formed AF tissue will be sufficient to support function following implantation and amenable to remodeling to reach a collagen content that approached that of native AF. More particularly the engineered biological material is characterized by lamellar sheets each composed of collagen fibres oriented parallel to each other and about 50-70°, more particularly 60-65°, most particularly 65° from the vertical. The engineered biological material may also comprise collagen, predominantly Type I collagen and types II, III, V, VI and type IX collagen are generally present in lesser amounts. In an embodiment an engineered biological material of the invention comprises in combination a fibrous scaffold of the invention and a continuous layer of annulus fibrosus tissue, preferably on the scaffold.

In an embodiment, the invention provides an engineered biological material comprising in combination annulus fibrosus tissue and a fibrous scaffold for the annulus fibrosus tissue, the annulus fibrosus tissue being reconstituted on the fibrous scaffold in vitro from isolated annulus fibrosus cells and being a continuous layer comprising annulus fibrosus cells and an extracellular matrix.

In an aspect the invention provides a process for producing an engineered biological material comprising: forming a layer of isolated annulus fibrosus cells on a fibrous scaffold of the invention, and; culturing the annulus fibrosus cells in culture media so that the annulus fibrosus cells accumulate extracellular matrix and form a continuous layer of annulus fibrosus tissue.

In another aspect, the invention provides a process for producing an engineered biological material of the invention comprising isolating annulus fibrosus cells from intervertebral disc; forming a layer of the annulus fibrosus cells on a fibrous scaffold, and; culturing the annulus fibrosus cells in culture media under suitable conditions so that the annulus fibrosus cells accumulate extracellular matrix and form annulus fibrosus tissue, in particular a continuous layer of annulus fibrosus tissue. In an embodiment the fibrous scaffold is a nanofiber porous scaffold comprising polyurethane and optionally ADO, in particular a polycarbonate urethane polymer and ADO.

The invention also relates to annulus fibrosus tissue derived from the engineered biological materials of the invention. Still further the invention contemplates an intervertebral disc construct comprising annulus fibrosus tissue derived from an engineered biological material of the invention.

The cells (e.g. annulus fibrosus cells) in engineered biological materials or constructs of the invention may be transformed with recombinant vectors containing an exogenous gene encoding a biologically active protein that corrects or compensates for a genetic deficiency, or stimulates cell growth or stimulates extracellular matrix production by cells, or alternatively, encoding a drug. Therefore, the invention also contemplates an engineered biological material or construct of the invention wherein cells (e.g. annulus fibrosus cells) in the engineered biological material or construct are transformed with recombinant vectors containing an exogenous gene encoding a biologically active protein which can correct or compensate for a genetic deficiency or have a stimulatory effect, or encoding a drug.

The invention still further relates to a system for testing a substance or agent that affects a soft tissue (e.g. annulus fibrosus tissue) comprising: generating and/or culturing an engineered biological material or construct of the invention comprising the soft tissue in the presence of a substance or agent which is suspected of affecting the soft tissue (e.g. annulus fibrosus tissue), and comparing the biochemical composition and/or physiological organization of the soft tissue with the biochemical composition and/or physiological organization of the soft tissue of the engineered biological material or construct generated and/or cultured in the absence of the substance or agent to determine its effect on the tissue.

The invention still further relates to a method of using the biological materials, tissues therefrom or constructs of the invention to test pharmaceutical preparations for efficacy in the treatment of diseases of intervertebral disc.

Still another aspect of the present invention provides a method of conducting a drug discovery business comprising:
  (a) identifying agents that affect the biochemical composition and/or physiological organization of an engineered biological material or tissues thereof, or a construct of the invention;
  (b) conducting therapeutic profiling of agents identified in step (a), or further analogs thereof, for efficacy and toxicity in animals; and
  (c) formulating a pharmaceutical preparation including one or more agents identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

Yet another aspect of the invention provides a method of conducting a target discovery business comprising:

(a) providing one or more engineered biological material, tissues therefrom or a construct of the invention for identifying agents by their ability to affect the biochemical composition and/or physiological organization of the engineered biological material, tissues therefrom or construct;

(b) (optionally) conducting therapeutic profiling of agents identified in step (a) for efficacy and toxicity in animals; and (c) licensing, to a third party, the rights for further drug development and/or sales for agents identified in step (a), or analogs thereof.

The invention provides methods of using an engineered biological material or tissues obtained therefrom or construct of the present invention as an implant to replace or repair damaged, degenerated or deficient soft tissues, in particular AF tissue or intervertebral discs or portions thereof, and methods for repairing damaged or degenerated soft tissues, in particular AF tissue or intervertebral discs or portions thereof. Methods of the invention may be used to treat vertebrates suffering from degenerated intervertebral disc conditions, and in particular to treat humans with such conditions.

Therefore, the invention contemplates a method of replacing or repairing damaged, degenerated or deficient AF tissue or intervertebral discs or portions thereof (preferably AF) of a patient comprising implanting an engineered biological material (or tissue therefrom) or construct of the invention into the site of the damaged, degenerated or deficient AF tissue or intervertebral disc of the patient. Methods for enhancing healing of an intervertebral disc in a patient are contemplated which comprise inserting an engineered biological material (or tissue therefrom) or construct of the invention into the site of a damaged intervertebral disc.

In an embodiment, the invention provides a method for replacing or repairing a degenerated or damaged annulus fibrosus tissue of an intervertebral disc comprising implanting in the disc space, after the removal of the degenerated or damaged annulus fibrosus tissue, an engineered biological material of the invention comprising a continuous layer of annulus fibrosus tissue, or annulus fibrosus tissue obtained therefrom.

In another aspect of the invention, a method for repairing damaged or degenerated intervertebral discs is provided comprising evacuating tissue from the annulus fibrosus portion of a degenerated intervertebral disc space, preparing an engineered biological material of the invention using annulus fibrosus cells from the evacuated tissue, and implanting the biological material or tissue therefrom in the evacuated annulus fibrosus space.

The invention also contemplates methods for using the engineered biological materials and tissues and cells therefrom, and constructs of the invention in gene therapy.

A biological material or construct of the invention can be used as an in vitro model for investigating the metabolism and degeneration of soft tissue and cells, in particular annulus fibrosus cells and tissues.

These and other aspects of the present invention will become evident upon reference to the following detailed description and attached drawings.

DESCRIPTION OF THE DRAWINGS

The invention will be better understood with reference to the drawings in which.

DETAILED DESCRIPTION OF PREFERRED EMBODIMENTS OF THE INVENTION

Formulations, Substrates and Scaffolds

Figure 1:
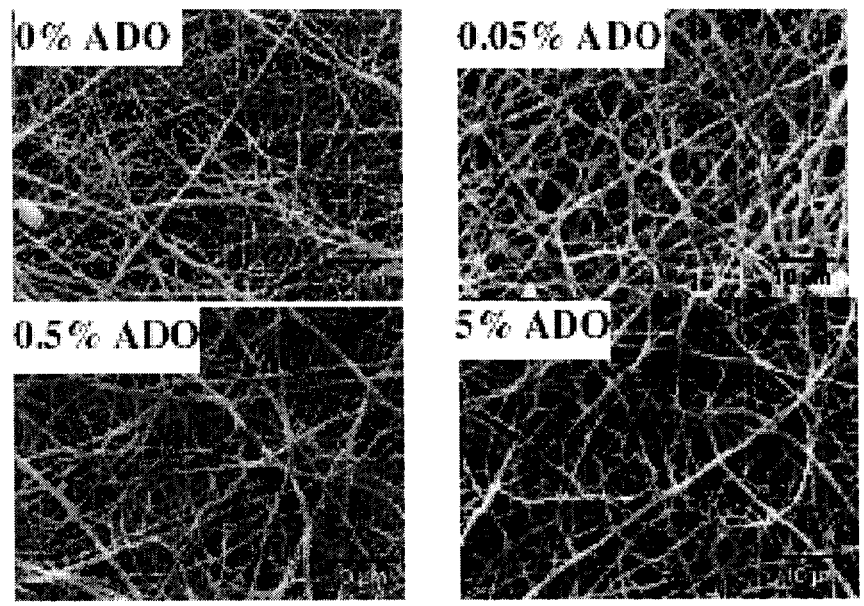
FIG. 1 shows SEM images of polycarbonate urethane fibrous scaffolds in the absence (0% ADO) or presence of increasing amounts of ADO (×5000 magnification).

The present invention provides fibrous scaffolds or substrates comprising polymer formulations prepared in nano-fibre form so as to promote the formation of soft tissues, including without limitation tendons, ligaments, fibrocartilage, intervertebral disc, articular cartilage, in particular nucleus pulposus tissue and annulus fibrosus tissue, more particularly annulus fibrosus tissue. Aspects of the invention provide novel polyurethane formulations for use in scaffolds or substrates for forming soft tissues. Particular aspects of the invention relate to selected formulations that specifically stimulate the growth of AF cells, in terms of cell growth, alignment, and/or collagen synthesis. Selected formulations influence protein adherence from culture media which influences cell activity in a manner which promotes tissue formation.

The present invention provides a class of polyurethane formulations processed into the form of nanofibres for use as a substrate or scaffold in soft tissue applications, in particular for preparing AF tissue.

In an aspect, the invention relates to a polyurethane formulation comprising polycarbonate urethane polymers characterized by one, two, three, four, five or six of the following properties:

a) It comprises a hydrolysable polyurethane chain which provides suitable mechanical properties to be applied in soft tissue applications, whereby the hard and soft segments of the polymer can be varied to optimize physical property requirements, ranging from rigid to elastomeric, in particular ranging from rigid plastic to elastomeric type materials.

b) It comprises polymers that can be blended with oligomers containing polar head groups (for example, the polar groups can be carboxylates, hydroxyls, amines, sulfonates, etc.) such that the polar function of such materials can be exposed to the outer surface layers.

c) It can be dissolved in dipolar solvents such as hexafluoro-2-propanol (HFP), which can be used in the formation of electro-spun fibre technology.

d) It can form distinct fibres, for example, as illustrated herein for a 5 wt % oligomer/polyurethane blend and a 0.05 wt % oligomer/polyurethane blend.

e) It is biodegradable.

f) It is biocompatible.

A polyurethane formulation contemplated herein comprising polyurethane polymers, in particular polycarbonate urethane polymers, may be prepared using conventional methods (e.g., Tang Y W, Labow R S, and Santerre J P, <<Enzyme-induced biodegradation of polycarbonate polyurethanes: Dependence on hard-segment concentration", J Biomed Mater Res 2001; 56: 516-528). In aspects of the invention, the process may comprise reacting a polyol [e.g. poly(1,6-hexyl 1,2-ethyl carbonate)diol] with a polyisocyanate (e.g, 1,6-hexane diisocyanate) under suitable conditions to permit polymer formation.

The polyol can be a macroglycol such as a hydroxyl-terminated polyester, polyether, polylactone or polybutadiene including without limitation a polytetramethylene oxide, a polycarbonate diol, a polyether with a high number of $CH_2$ groups between oxygen bridges or an aliphatic macroglycol. Examples of macroglycols include without limitation ethylene glycol, propylene glycol, 1,4-butanediol, hexanediol, 2-ethyl-1,6-hexanediol, neopentyl glycol and the like, cycloaliphatic glycols such as cyclohexanedimethanol, and aromatic-aliphatic glycols such as bis-1,4(β-hydroxyethoxy) benzene. In an aspect, the polyol is poly(1,6-hexyl 1,2-ethyl carbonate)diol.

The polyisocyanate can be a diisocyanate, for example, 1,6 hexane diisocyanate, lysine diisocyanate, diphenylmethane diisocyanate (MDI), toluoylene diisocyanate (TDI). tolylene diisocyanate, xylene diisocyanate, hexamethylene diisocyanate, isophorone diisocyanate, lysine diisocyanate, 2,2,4-trimethylhexamethylene diisocyanate, cyclohexylmethane diisocyanate, methylcyclohexane diisocyanate, isopropylidene-bis(4-cyclohexyldiisocynate) and hexamethylene diisocyanate/biuret, in particular 1,6 hexane diisocyanate.

In an aspect, the invention utilizes a polyurethane formulation comprising a blend of polyurethane polymers, in particular polycarbonate urethane polymers, and selected oligomers that increase surface energy in a scaffold or substrate formed from the formulation. The formulation is characterized by one or more of properties a) to f) above, preferably all of properties a) to f) above, and one or more the following properties:

g) The oligomers contain groups or features that can bond with the polyurethane chains in such a manner so as not to compromise the materials physical properties.

h) Concentrations of the oligomers within the polymer blend are less than about 5 wt %, preferably less than about 4 wt, 3 wt, 2 wt 1 wt, or 0.5 wt %, in order to achieve optimal cell adhesion properties, and are generally greater than 0.005 wt % and preferably as least 0.05 wt % in order to express advantageous properties over that of the polyurethane alone.

i) The polyurethane/oligomer blend dissolves in dipolar solvents such as hexafluoro-2-propanol (HFP), which is used in the formation of electro-spun fibre technology.

j) The polyurethane/oligomer blend can form distinct fibres, for example, as illustrated herein for a 5 wt % oligomer/polyurethane blend and a 0.05 wt % oligomer/polyurethane blend.

k) It has surface carboxylic acid groups.

l) It has a relatively hydrophobic central portion.

m) It has a hydrophobic terminal segment with urethane, carboxylic acid and hydroxyl groups.

n) It has significantly lower contact angles compared with a polyurethane formulation without the selected oligomers. In aspects of the invention, the contact angle value is between about 20° to 50°, 30° to 50°, 30° to 45°, 30° to 40°, 30° to 35°, 33° to 40° or 33° to 35°.

In aspects of the invention, the selected oligomers are novel anionic dihydroxyl oligomers (ADO). An anionic dihydroxyl oligomer may be synthesized by linking a polyether diol with a carboxylic ester in the presence of a polyisocyanate, and hydrolzying the resulting oligomeric product.

The polyisocyanate is preferably a diisocyanate, for example, lysine diisocyanate, diphenylmethane diisocyanate (MDI), toluoylenediisocyanate (TDI). tolylene diisocyanate, xylene diisocyanate, hexamethylene diisocyanate, isophorone diisocyanate, lysine diisocyanate, 2,2,4-trimethylhexamethylene diisocyanate, cyclohexylmethane diisocyanate, methylcyclohexane diisocyanate, isopropylidene-bis(4-cyclohexyldiisocyanate) and hexamethylene diisocyanate/biuret, in particular lysine diisocyanate.

The polyether diol can be a polybutylene glycol, polytetramethylene ether glycol, or a mixture thereof, in particular polybutylene glycol, more particularly poly(1,2 butylene glycol).

Examples of a carboxylic ester include acrylic esters and methacrylic esters such as methyl acrylate, ethyl acrylate, n-propyl acrylate, isopropyl acrylate, n-butyl acrylate, isobutyl acrylate, t-butyl acrylate, 2-hydroxyethyl acrylate, 2-hydroxypropyl acrylate, methyl methacrylate, ethyl methacrylate, n-propyl methacrylate, isopropyl methacrylate, 2-hydroxyethyl methacrylate, 2-hydroxypropyl methacrylate, n-butyl methacrylate, isobutyl methacrylate and t-butyl methacrylate. In embodiments of the invention, the carboxylic ester is a methacrylic ester, in particular 2-hydroxyethyl methacrylate or 2-hydroxypropyl methacrylate, more particularly 2-hydroxyethyl methacrylate.

In an embodiment, an ADO is characterized by one or more of the following properties:
  a) About 50% to about 70%, about 50% to 60% or about 55% to 65% of its side chains comprise carboxylic acid groups.
  b) Absorption bands in the about 600 $cm^{-1}$ to about 4000 $cm^{-1}$ region by FTIR.
  c) A peak corresponding to a urethane group at about 1680-1750 $cm^{-1}$, in particular 1720 to 1740 $cm^{-1}$, by FTIR.
  d) It is stable when blended with polyurethane polymers.

The polyurethane formulations can be fabricated into scaffolds or substrates, in particular fibrous scaffolds or substrates for growing soft tissues, in particular annulus fibrosus tissue. Fabrication can involve physical, chemical or thermal manipulation of the formulations. Scaffolds or substrates can be generated from the formulations by casting, roll mills, injection molding, or electrospinning, preferably electrospinning. Additives may be added to the formulations to facilitate processing, including solvents, fillers, pigments, antioxidants, US light stabilizers, and mold release agents. For example, solvents, in particular dipolar solvents such as hexafluoro-2-propanol can be added to a formulation to facilitate electrospinning. A fibrous porous scaffold or substrate can be sterilized using methods known in the art such as steam sterilization, ethylene oxide sterilization, and radiation.

A fibrous scaffold can comprise interconnecting randomly distributed pores. A fibrous scaffold of the invention can be random or the fibers can be aligned in the same direction.

In aspects of the invention, the fibres in the scaffold or substrate can have a thickness of between about 100 to about 1500 nm, 130 to about 1500 nm, 130 to about 1000 nm, 130 to about 890 nm, about 200 to about 600 nm, about 200 to 400 nm, or about 200 to about 350 nm, or an average fibre thickness of about 250-400 nm, about 250 to 300 nm, about 250 to 275 nm, or about 260 to about 275 nm.

In aspects of the invention the scaffold comprises 0.05 wt % to 5 wt %, 0.1 wt % to 2 wt %, 0.2 wt % to 1 wt %, or 0.2 wt % to 0.75 wt % oligomers, preferably 0.5 wt % oligomers (e.g. ADO).

Specific formulations can be selected to generate scaffolds or substrates, in particular biodegradable biocompatible polyurethane scaffolds or substrates, that promote annulus fibrosus cell adherence in an oligomer dependent manner. In aspects of the invention, a formulation comprising oligomer (e.g. ADO) concentrations between 0.05 and 5 wt % provides advantageous or optimal cell adhesion (see FIG. 5). This optimized behaviour preferably results from employing nano formed substrates and polar head chemistry embedded within the material in such a manner that the oligomers are stable over the time period of cell culture. The formulations can produce optimized conditions for the synthesis of new collagen and enhanced retention of total collagen tissue.

Formation of Soft Tissues Exemplified by Annulus Fibrosus Tissue

In an aspect, the invention relates to an engineered biological material comprising a fibrous scaffold of the invention and a continuous layer of annulus fibrosus tissue on the scaffold. The annulus fibrosus cells are characterized by being capable of synthesizing collagen, in particular Type I collagen, in similar amounts and organization as in annulus fibrosus cells in vivo. The annulus fibrosus tissue is further characterized by having a three dimensional organization that is characteristic of annulus fibrosus tissue, either single lamella or ultimately an entire annulus fibrosus, in vivo.

The invention also relates to a method for producing an engineered biological material comprising isolating annulus fibrosus cells of intervertebral disc; forming a layer of the cells on a fibrous scaffold of the invention; culturing the cells in growth or culture media under suitable conditions so that the cells accumulate intracellular matrix and form a continuous layer of annulus fibrosus tissue, single lamella.

The cells used in the method of the invention may be isolated from intervertebral discs (IVD) (lumbar discs, thoracic discs, or cervical discs) from animals, preferably humans, bovines, ovines, rabbits, most preferably humans. The tissue may be isolated from adult or fetal tissue. In one embodiment of the invention, the cells are isolated from intervertebral disc of the lumbar spine of sheep. Intervertebral disc tissue may be extracted from a patient being treated, or alternatively from a donor, using known surgical techniques. The annulus fibrosus cells may be isolated from intervertebral disc tissue by sequential enzyme digestion to techniques, such as those described in Boyle et al, Osteoarthritis and Cartilage 3, 117-125, (1995). For example, the cells may be treated with 0.5% protease followed by 0.1% bacterial collagenase.

A continuous layer of cells is preferably placed on a fibrous scaffold of the invention. Annulus fibrosus cells may be seeded on a selected substrate at a cell density of about $1 \times 10^4$ to $0.1 \times 10^6$ cells/$cm^2$, $1 \times 105$ to $0.1 \times 10^6$ cells/$cm^2$, preferably $0.1$-$1 \times 10^6$ cells/$cm^2$, more preferably $0.5 \times 10^6$ cells/$cm^2$ or $5 \times 10^5$ cells/$cm^2$. The cells seeded on a coated or uncoated substrate are grown in suitable culture conditions. Examples of suitable culture media are known in the art, such as Hams F12 and/or Dulbecco's modified Eagle's medium (DMEM). The culture medium may contain serum, for example, heat inactivated fetal bovine serum in a concentration range of about 2-20%, preferably 10-20%, and may further contain growth factors and ascorbic acid. The cells may be cultured at 37° C. in a humidified atmosphere supplemented with $CO_2$. The cells may be cultured for 1-5 weeks, or for a greater or less time, to obtain a product which may be suitable for some uses such as transplantation or gene therapy.

In an embodiment of the invention, isolated AF cells (e.g. at a density of $0.5 \times 10^6$/40 µL) are grown in HAMs F12 supplemented media containing 5% fetal bovine serum for about 7 days.

Mechanical force(s) may be administered during in vitro formation of the engineered biological material in order to enhance the development of tissues that are highly suited for implantation and physiological weight bearing. Torsion, compression, and/or shear forces may be applied during tissue formation. Forces, together or alone, may be applied, consecutively, simultaneously, or cyclically. The mechanical forces may be applied through the use of a mechanical stimulation system that allows for loading cell cultures under sterile conditions. For example, the Mach-1™ system (Biosyntech, Montreal) is capable of supplying simultaneous compressive and linear shear forces, and can include the application of torsional shear forces. For each type of force application, a skilled artisan can determine the optimal conditions to induce tissue growth and organization (i.e. force amplitude, frequency and duration of stimulation).

In an embodiment of the invention, either sinusoidal compressive or torsional forces are applied to the developing tissue. Compressive forces may be applied at about day 3, in a range of unconstrained loading between 0.1 to 10 N (approximately corresponding to compressive stresses of 0.01 to 1 MPa), through a compliant, biocompatible, autoclavable elastomer (e.g. medical grade silicone or polyurethane) placed on the actuator to avoid direct contact with the cells. The duration of loading may range from 100 to 1200 cycles/day and may be applied at a frequency of 1.0 Hz. (1 Hz approximates normal gait frequency of disc loading). Minimal numbers of loading cycles may be preferred to stimulate organization of IVD tissues or components thereof (e.g., annulus fibrosus tissue or cells). For example, 20 sec. of 1 MPa of hydrostatic pressure may be sufficient to stimulate proteoglycan synthesis by inner annulus cells.

Torsional shear force application may consist of a compressive preload followed by varying degrees of cyclic torsional shear. Angular deformation amplitudes ranging from 0.005 rad to 0.05 rad at a frequency of 1 rad/sec, may be used (approximately corresponding to a maximal torque of 0.5N.mm). Cyclic compressive and torsional shear forces may be simultaneously applied.

The invention also contemplates an intervertebral disc construct. The construct may comprise annulus fibrosus tissue, with cartilagenous tissue and/or a substrate (e.g. an engineered bone substitute). In an embodiment, the construct comprises an engineered bone substitute with cartilagenous tissue formed thereon, and AF tissue derived from an engineered biological material of the invention fused to the bone substitute-cartilagenous tissue. This construct may be prepared by culturing articular chondrocytes on porous calcium polyphosphate (CPP) discs for about 3 weeks using the methods described in U.S. Pat. No. 5,326,357. Simultaneously, AF cells may be grown on a fibrous substrate or scaffold of the present invention. At about 1-2 weeks, a piece of AF tissue formed in vitro may be punched out from the substrate or scaffold, and placed on the CPP-cartilagenous tissue construct. The tissue components may be held together using fibrin glue, or other suitable adhesive, and maintained in culture for a sufficient period of time, e.g. about 2-6 weeks, 2-4 weeks, or 3-4 weeks, in particular about 3 weeks. The composite may be harvested to form the construct.

In another embodiment of the invention, the construct resembles a natural disc. Articular cartilage tissue may be cultured in a depression of a substrate using the methods described in U.S. Pat. No. 5,326,357 or U.S. Pat. No. 6,077, 989. Annulus fibrosus tissue derived from an engineered biological material of the invention (or other source) may be grown on the cartilagenous tissue formed on the substrate. After fusion of the annulus fibrosus and cartilagenous tissues, a plug of annulus fibrosus tissue may be removed from the centre of the annulus fibrosus tissue and replaced with nucleus pulposus tissue (see WO02/00142). The resulting composite comprising annulus fibrosus, nucleus pulposus, cartilage endplate, and substrate is grown in culture to produce a construct comprising fused annulus fibrosus tissue, nucleus pulposus tissue, and cartilage tissue, with a substrate.

The engineered biological material, tissues therefrom and constructs of the present invention can be used as model systems for in vitro studies of intervertebral disc (or components thereof i.e. annulus fibrosus tissue or nucleus pulposus tissue) function and development.

In accordance with one embodiment of the invention, an engineered biological material may be used to test substances which affect intervertebral disc or components thereof (e.g. annulus fibrosus tissue). A system for testing a substance that affects intervertebral disc or components thereof in accordance with the invention comprises generating or culturing an engineered biological material or construct of the invention comprising intervertebral disc tissue, in particular AF tissue, in the presence of a substance which is suspected of affecting intervertebral disc or components thereof, and determining the biochemical composition and/or physiological organization of the tissue of the engineered biological material or construct, and comparing with the biochemical composition and/or physiological organization of tissue of the engineered biological material or construct in the absence of the substance.

The substance may be added to the culture or the cells in the engineered biological materials (e.g., annulus fibrosus cells) may be genetically engineered to express the substance, i.e. the cells may serve as an endogenous source of the substance. Cells may be engineered by viral or retroviral-mediated gene transfer using methods known in the art to produce a specific substance. The engineered cells are constructed and maintained such that they release the substance into the medium for the desired period of time for the culture.

The system may be used to analyze the effects of substance (s) on different stages of soft tissue development, in particular intervertebral disc development or components thereof (e.g., annulus fibrosus tissue). Effects on cells at very early, intermediate, and late stages of development may be evaluated by assessing the cells and the biochemical composition and/or physiological organization of the tissue generated in the cultures at various times such as 2, 4, 6 and 8 weeks.

The biochemical composition and/or physiological organization of the tissue generated in the cultures may be assessed using the methods described herein (e.g., DNA content, cell morphology, proteoglycan content, and collagen content). In an embodiment of the invention, the biological materials of the present invention may be used in the testing of pharmaceutical preparations useful in the treatment of diseases of soft tissues, for example, intervertebral disc.

The biological materials of the invention may also be implanted into patients to replace or repair damaged, degenerated or deficient soft tissue, for example, intervertebral disc or components thereof (e.g. annulus fibrosus tissue). In particular, the biological materials of the invention may be implanted into individuals with idiopathic scoliosis, herniated disc, degenerative disc disease, recurrent disc herniation, or spinal stenosis.

It is also contemplated that the biological materials of the present invention can be used to enhance healing of damaged, degenerated or deficient intervertebral discs when inserted into the site of the disc.

The invention also contemplates using the engineered biological materials of the invention in gene therapy. Therefore, recombinant vectors containing an exogenous gene encoding a biologically active protein that is selected to modify the genotype and/or phenotype of a cell to be infected may be introduced into cells (e.g. annulus fibrosus cells) in the engineered biological materials of the invention. An exogenous gene coding for a biologically active protein which corrects or compensates for a genetic deficiency or a drug may be introduced into cells in the engineered biological materials. For example, IGF-I could be introduced into the cells so that the cells secrete this protein and stimulate production of proteoglycans resulting in disc regeneration. The expression of the exogenous gene may be quantitated by measuring the expression levels of a selectable marker encoded by a selection gene contained in the recombinant vector.

The following non-limiting examples are illustrative of the present invention:

Example 1

Degenerative disc disease is associated with the development of low back pain. Using annulus fibrosus (AF) tissue formed in vitro on polymeric scaffolds to replace damaged native tissue is a novel approach to the treatment of this disease. In this study, a series of biodegradable polycarbonate urethane nano-fibres with controlled change in surface energy were generated to assess their use as scaffolds for AF tissue formation. Polycarbonate urethane (PU) was chosen for its biodegradability and biocompatibility.

Materials and Methods

Polymer synthesis: A novel anionic divinyl oligomer (ADO) bearing —COOH group was synthesized through the reaction of polytetramethylene oxide, hydroxyethylmethacrylate and lysine diisocyanate in dimethyl acetamide (DMAC) solvent overnight at 50-60° C. The ester groups on the lysine were hydrolyzed to carboxylic acid groups. PU was used as the base polymer for scaffold fabrication, and it was synthesized as described previously [Tang Y W, et al. J Biomed Mater Res 2001; 56: 516-528].

Contact angle measurement: PU alone or with various concentrations of ADO ranging from 0.05 to 5% (wt %) were dissolved in pyridine and cast on glass cover slips to form smooth films. The water contact angle on flat films was measured using a Rame-hart contact angle goniometer.

Formation of nano-fibrous scaffolds: PU or PU containing 0.05, 0.5 or 5% (wt %) ADO were dissolved in 1,1,1,3,3,3-hexafluora-2-propanol. The polymer solution was electrospun at 0.5 ml/hr and 1000 volt/cm electrostatic force at room temperature. The porous scaffolds were prepared for scanning electron microscopy (SEM) examination.

AF cell culture: IVDs were harvested from bovine caudal spines and the AF tissue was separated out. AF cells were isolated by sequential enzymatic digestion and seeded onto fibrous scaffolds under static conditions at a cell density of $0.5 \times 10^6/40$ μL. The cells were grown in Hams F12 supplemented with 5% fetal bovine serum. To determine the role of protein adsorption on cell attachment to the different scaffolds, in selected cultures the cells were either cultured serum-free or preincubated in cycloheximide and then seeded in serum-free media supplemented with cycloheximide (10 μg/mL). To quantify cell attachment the cell-seeded scaffolds were papain digested for 48 hours at 65° C. and DNA content was determined using Hoescht 33258 dye binding assay and fluorometry. The percent cell attachment to the scaffolds was determined by dividing the DNA content of the cell seeded scaffolds at 24 hours by the DNA content of the cell aliquot used to seed the scaffold.

AF cell morphology: Cells were cultured on scaffolds for 24 or 48 hours, harvested and processed for SEM examination.

Statistical analysis: The results were expressed as the mean±SEM and analyzed by ANOVA and Scheffe's test. Differences were considered significant at $p<0.05$.

Results

Contact angle measurement: The contact angle of PU alone was 52.81±0.60 and this decreased significantly with increasing ADO content in the PU/ADO mixtures up to 5% (33.05±1.390).

Appearance of fibrous scaffolds: SEM (FIG. 1) showed that fibrous scaffolds were fabricated from PU as well as from PU containing different amounts of ADO. The fibre diameter of the different polymeric scaffolds ranged from 100 nm to 1 μm and did not appear to be affected by the amount of ADO in the polymer mixture. All scaffolds were similar in appearance.

Figure 2:
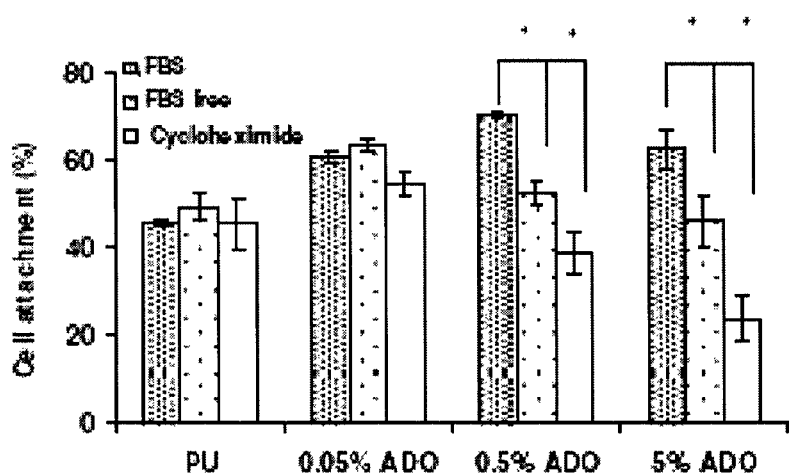
FIG. 2 is a graph showing AF cell attachment to scaffolds in the presence of serum (5% FBS), serum free, or serum-free media with cycloheximide. * indicates significant difference.
Figure 3:
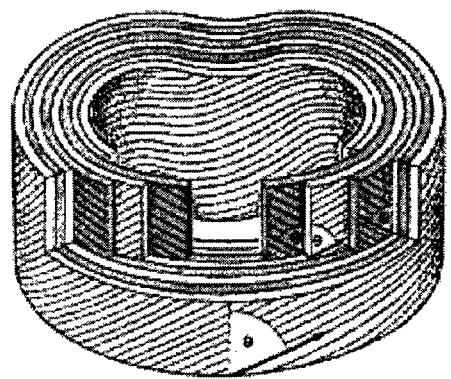
FIG. 3 is a diagram showing annulus fibrosus tissue structure.
Figure 4:
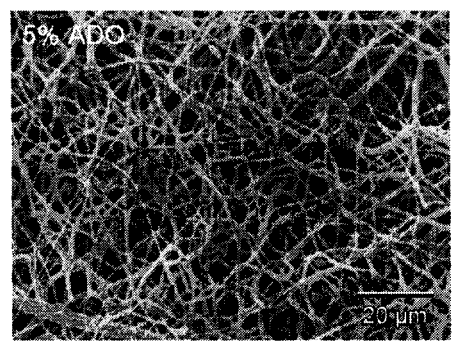
FIGS. 4A and B show SEM images of random polycarbonate urethane fibrous scaffold with 5% ADO and 0.05% ADO.
Figure 4:
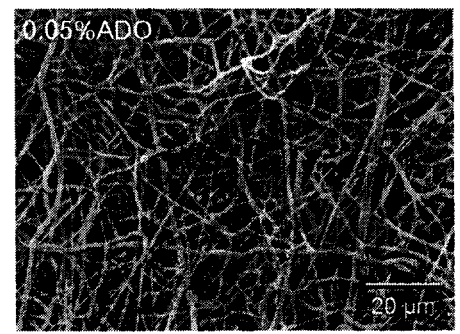
Figure 5:
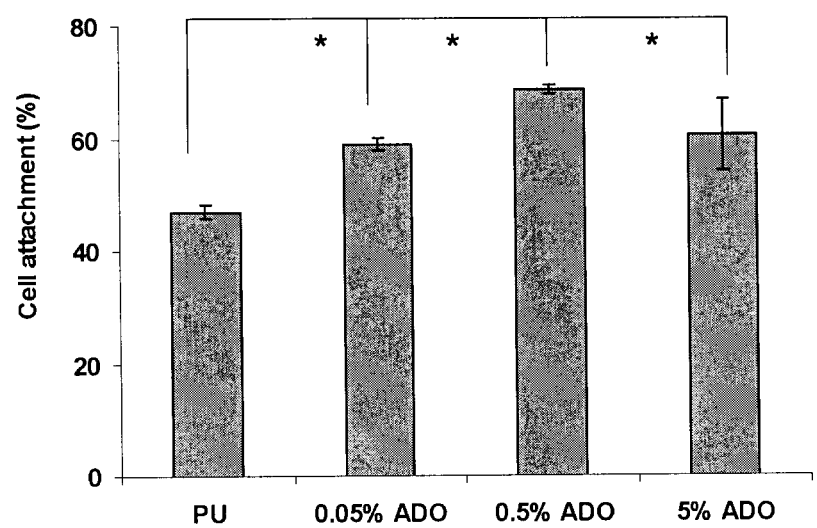
FIG. 5 is a graph showing AF cell attachment to poly carbonate urethane fibrous scaffolds with 0.05% ADO, 0.5% ADO, 5% ADO and without ADO. * indicates significant difference.
Figure 13:
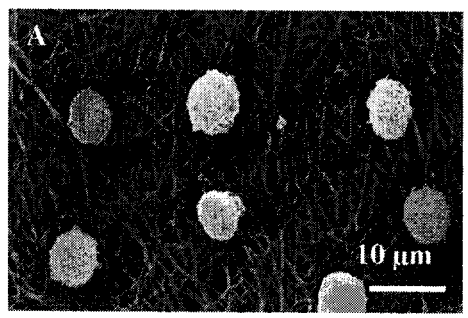
FIG. 13 shows SEM images of AF cells attached onto PU scaffolds containing (A) 0%, (B) 0.05%, (C) 0.5%, and (D) 5% ADO 24 hours after cell seeding.
Figure 13:
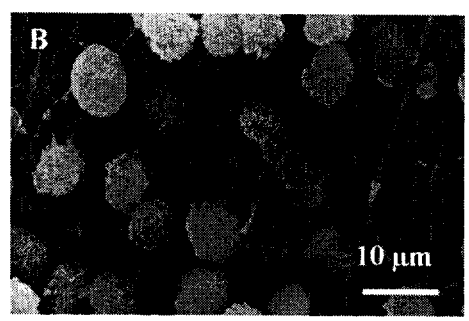
Figure 13:
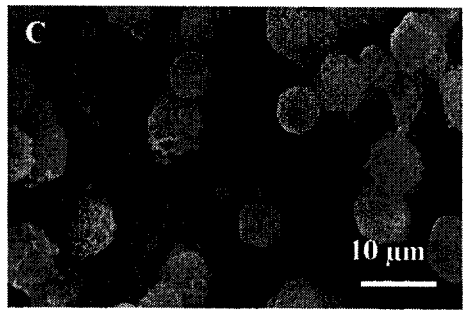
Figure 13:
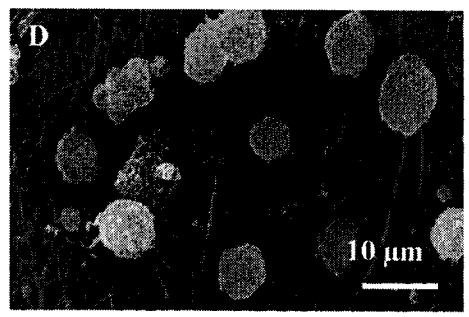

AF cell attachment: Significantly more AF cells attached to ADO containing PU scaffolds when compared to the PU scaffold alone. Increasing the ADO content from 0.05% to 0.5% further enhanced AF cell attachment but this effect reached a plateau as no further increase was observed for scaffolds containing 5% ADO (FIG. 5). SEM demonstrated that the attached cells remained round and there was no difference in the appearance of the cells attached to the different scaffolds up to 48 hours of culture (FIGS. 13 and 4). Seeding cells serum-free in the presence or absence of cycloheximide did not affect cell attachment to scaffolds made from PU alone or PU with 0.05% ADO (FIG. 2). However, these conditions for 0.5% and 5% ADO scaffolds inhibited cell attachment with the greatest inhibition observed under serum-free conditions with cycloheximide (FIG. 2).

Discussion

This study demonstrates that electrospinning can be used to generate nanofiber porous scaffolds made from PU alone or PU with various amounts of ADO. AF cells attached to the different scaffolds and there was no difference in the morphology of the cells. Increasing the amount of ADO up to 5% decreased the water contact angle, indicating that the addition of ADO increased surface energy. Scaffolds containing 0.05% ADO had greater cell attachment than scaffolds made of PU alone. This was attributed to the increased surface energy, as similar numbers of cells attached in the absence or presence of proteins present in the serum or made by the cell (serum-free in presence of cycloheximide). There was increased cell attachment as the surface energies increased above 0.5 wt % ADO, only in the presence of serum and proteins made by the cells. This suggests that surface energy positively affects cell adhesion likely through its influence on protein adsorption onto the scaffold, as in the absence of serum and new protein synthesis (presence of cycloheximide) there was decreased cell attachment with increasing ADO content from 0.05% ADO to 5% ADO ($p<0.05$). This decrease in cell attachment may be due to increasing electrostatic repulsion between the cell membrane and the negatively charged scaffold. Both serum and cell synthesized proteins contribute to cell attachment.

Example 2

Figure 6:
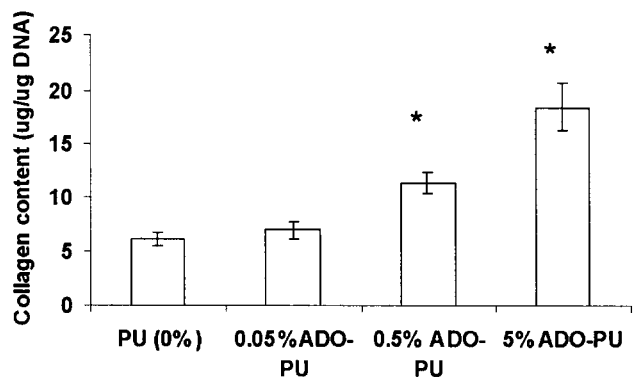
FIG. 6 shows the following: (A) graph showing collagen content of tissue formed by AF cells cultured on fibrous scaffolds comprising polyurethane (PU), 0.05% ADO-PU, 0.5% ADO-PU, and 5% ADO-PU. (B) A graph showing retained and newly synthesized collagen of AF cells cultured on fibrous scaffolds comprising polyurethane (PU), 0.05% ADO-PU, 0.5% ADO-PU, and 5% ADO-PU. (C) SEM image taken on a cross-section showing layers of tissue formed on the scaffold containing 0.5 wt % oligomer.
Figure 6:
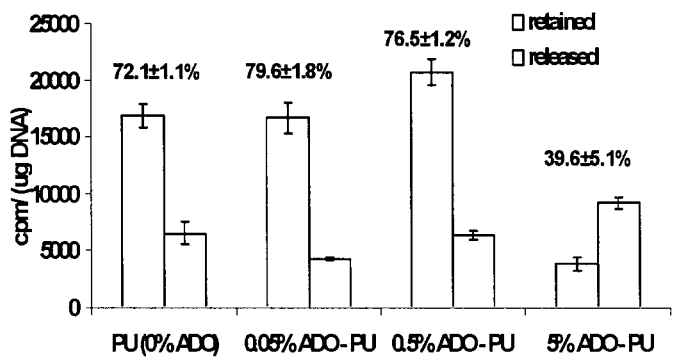
Figure 6:
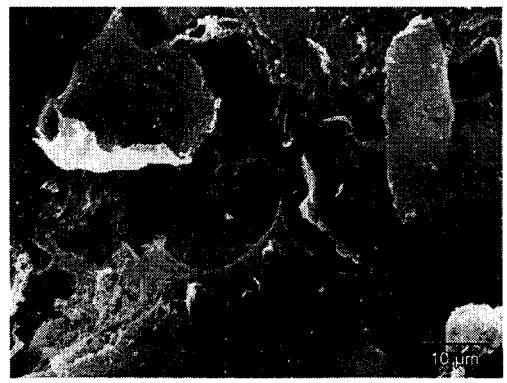

AF cells were isolated from bovine caudal discs, seeded ($0.5 \times 10^6$) onto fibrous scaffolds, and cultured in Hams F12 with 20% FBS for 7 days. Accumulation of collagen content over 7 days of culture was determined by performing a hydroxyproline assay. Collagen synthesis was quantified by incubating the cells with [$^3$H]-proline (2 μCi/sample) for 24 hours on day 7 of culture and determining the amount of radioactivity incorporated. The results showed that significantly more collagen was produced and accumulated in a week by cells grown on polyurethane scaffolds containing 0.5 wt % and 5 wt % oligomer (FIG. 6A), while on day 7 the newly synthesized and retained collagen on polyurethane scaffold with 0.5 wt % oligomer was nearly twice as much as that on the scaffold containing 5 wt % oligomer (FIG. 6B). An SEM image (FIG. 6C) taken on a cross-section showed that there were a few layers of tissue formed on the scaffold containing 0.5 wt % oligomer.

Example 3

Synthesis of ADO and Scaffolds

Synthesis of anionic dihydroxyl oligomer (ADO) An anionic dihydroxyl oligomer was synthesized using lysine diisocyanate (LDI) as a coupling agent to combine polybutylene glycol (PTMO, Aldrich) with hydroxyethylmethacrylate (HEMA; Aldrich, Milwaukee, Wis.). Before synthesis, LDI and HEMA were distilled under vacuum whereas PTMO was degassed overnight under vacuum at 40° C. The PTMO was dissolved in DMAC and reacted with LDI in a 3:4 molar ratio with 0.01 mL of DBDA at 65° C. for 4 hrs. The concentration of total reactants in the first step was 20% (w/v). This was then followed by the addition of distilled HEMA along with 0.01 mL of DBDA. HEMA was used here as a temporary blocking group during the termination of the oligomer synthesis. This ending step progressed for 4 h in a temperature range of 60-70° C. The final mixture was left to stir overnight between 50-60° C. The oligomeric product was precipitated into ether/distilled water solution (30/70 v/v), washed and dried.

8 mmol of dried oligomer was then dissolved in 100% methanol followed by the addition of 40 mL NaOH/MeOH (0.1 N) to hydrolyze the ester group on LDI side chain. The hydrolysis process was allowed to run at room temperature for 18 hours, after which 250 mL citric acid water solution (3.4% wt/v) was added to convert carboxylate sodium salt to carboxylic acid. To help precipitate the hydrolyzed product, an appropriate amount of KCl powder was directly added to the solution. The top clear aqueous solution was poured out and fresh distilled water was added in to dissolve and remove KCl. After repeating this step three times, the least amount of acetone was added to dissolve the product and then the large quantity of distilled water was gradually dripped in to precipitate the final product. The product was then vacuum dried at room temperature for one day followed by drying at 40° C. for two days.

PU alone and with the oligomer at 3 different concentrations (e.g. 0.05 wt %, 0.5 wt % and 5 wt %) were blended together to reach a total concentration of 20 wt % in 1,1,1,3,3,3-hexafluoro-2-propanol (HFIP, Aldrich) and mechanically stirred at room temperature until reaching clear solution. Formation of random scaffolds: The electrospinning conditions were optimized based on the concentration of polymer solution, distance between the nozzle and collector, flow rate of polymer solution and voltage applied to polymer solution. In brief, a 20 wt % polymer solution was fed by a syringe pump (PHD 2200, Harvard Apparatus) into an 18" stainless steel needle suspended vertically 15 cm above an aluminum collector plate. A high-voltage generator (Gamma High-Voltage Research) was employed with a high positive voltage (15 kV) to charge the steel needle containing the polymer solution. Aluminum collector plate was grounded to allow deposition of fibers, leading to formation of a random fibrous porous scaffold.

Figure 7:
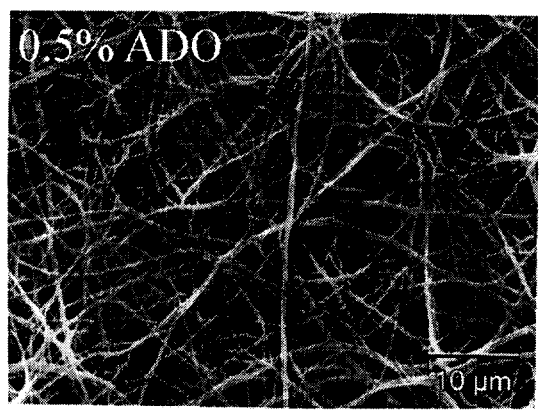
FIG. 7 shows SEM images of (A) a random fibrous porous scaffold made of polyurethane with 0.5% wt oligimer and (B) aligned fibrous porous scaffold made of polyurethane with 0.5% wt oligimer.
Figure 7:
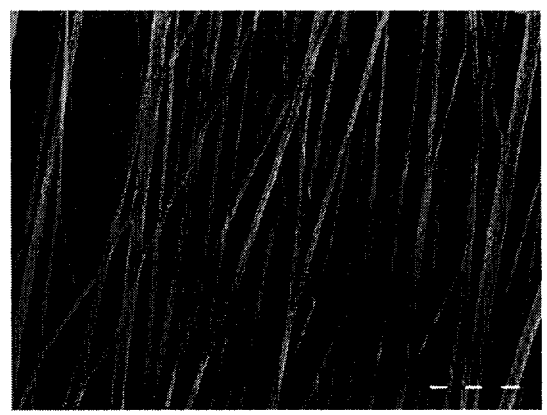

Formation of aligned scaffolds: To get fibers aligned in the same direction, a rotating mandrel was machined to be used as a collector to replace the aluminum collector. To obtain aligned fibers, rotating speed of this mandrel was optimized to be 627 m/s while all other conditions stay the same as mentioned. (See FIG. 7.)

Figure 8:
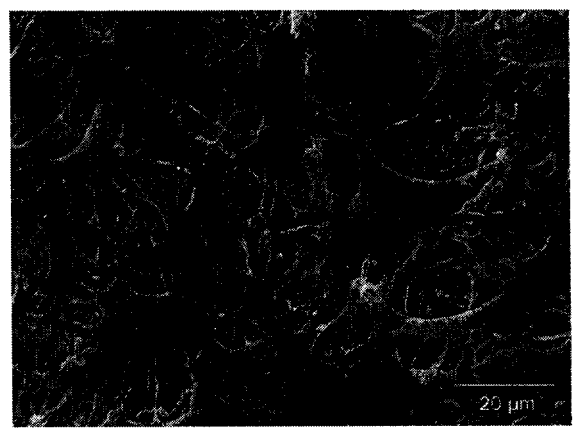
FIG. 8 shows SEM images of cells grown on (A) a random scaffold for 5 days and (B) cells grown on an aligned scaffold for 5 days.
Figure 8:
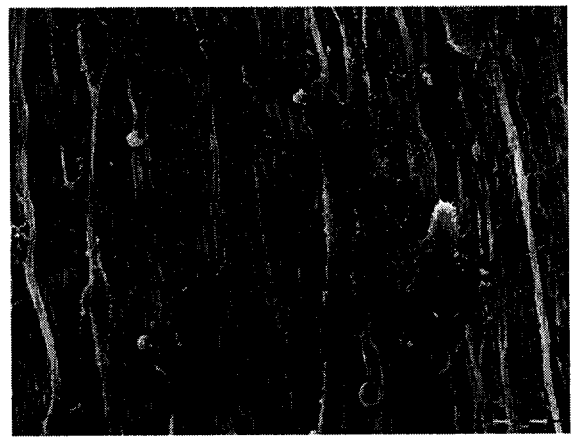

Cell response to random and aligned scaffolds in terms of cell morphology: AF cells were seeded on an aligned fibrous PU scaffold containing 0.5% ADO and were cultured for 5 days. It was observed that cells could sense the major direction of fibers and responded by spreading along the orientation of fibers, whereas cells grown on random scaffolds showed a pancake-like morphology. (See FIG. 8.)

Example 4

The following materials and methods were used in the studies described in this example.
Materials and Methods
Polycarbonate urethane synthesis: A polycarbonate urethane (PU) was used as the base polymer in this study, because it is biodegradable, biocompatible and its synthesis is easily reproducible. The polymer was synthesized using a conventional two-step procedure [39] in a controlled atmospheric glove box under dried nitrogen gas. Briefly, poly(1,6-hexyl-1,2-ethyl carbonate) diol (PCN, Aldrich, Miwaukee, Wis.) was degassed and dissolved in anhydrous N, N-dimethylacetamide (DMAC) (Aldrich) (30% w/v) at 65° C. and then reacted with distilled 1,6-hexane diisocynanate (HDI, Miwaukee, Aldrich) in the presence of 0.3 wt % dibutyltin dilaurate (DBDA, Aldrich) (relative to the total mass of all synthesis reactants). The prepolymer reaction temperature was maintained between 60°-70° C. for 4 hrs before the addition of 1,4-butanediol (BD, Aldrich) with 0.1 wt % DBDA. The chain extension step proceeded for 2 h with the temperature set between 60° and 70° C. The final reaction solution was then allowed to stir overnight at room temperature. The polymer was precipitated in an ether/water solution (30% v/v) to wash out the residual DBDA and low molecular weight oligomer. The polymer was subsequently washed in five changes of water (3 hr each wash) and dried under vacuum for 72 hrs.

Synthesis of anionic dihydroxyl oligomer (ADO): The anionic dihydroxyl oligomer was synthesized using lysine diisocyanate (LDI) as a coupling agent to link polybutylene glycol (PTMO, Aldrich, Milwaukee, Wis.) with hydroxyethylmethacrylate (HEMA; Aldrich, Milwaukee, Wis.). Prior to synthesis, LDI and HEMA were distilled under vacuum and PTMO was degassed overnight under vacuum at 40° C. The PTMO was dissolved in DMAC and reacted with LDI in a 3:4 molar ratio with 0.01 mL of DBDA at 65° C. for 4 hrs. The concentration of total reactants in the first step was 20% (w/v). This was then followed by the addition of distilled HEMA along with 0.01 mL of DBDA. HEMA was used here as a temporary blocking group during the termination of the oligomer synthesis. This termination step progressed for 4 h, while maintaining the temperature in a range of 60-70° C. The final mixture was stirred overnight between 50-60° C. The oligomeric product was precipitated into ether/distilled water solution (30/70 v/v), washed and dried.

8 mmol of dried oligomer was then dissolved in 100% methanol followed by the addition of 40 mL NaOH/MeOH (0.1 N) to hydrolyze the ester group on LDI side chain and the esters associated with the HEMA. The hydrolysis reaction was allowed to run at room temperature for 18 hours, after which 250 mL citric acid water solution (3.4% wt/v) was added to convert the carboxylate sodium salt to a carboxylic acid. To help precipitate the hydrolyzed product, an appropriate amount of KCl powder was directly added to the solution. The top clear aqueous solution was decanted and fresh distilled water was added to dissolve and remove KCl. After repeating this step three times, acetone was added to dissolve the product producing a saturated solution then distilled water was gradually added dropwise to precipitate the final product which was then vacuum dried at room temperature for one day followed by drying at 40° C. for two days.

Characterization of ADO: To quantify the amount of carboxylic acid group in the hydrolyzed oligomer, 0.3 gram of the oligomer was dissolved in 10 ml toluene/acetone (2:1 v/v) solvent mixture. Two drops of phenolphthalein were added and the solution was titrated with a 0.025 N NaOH/methanol solution (calibrated with a commercial HCl aqueous standard). This was repeated three times. The —COOH number was reported as moles of COOH/gram of ADO.

Structure confirmation: The synthesized anionic dihydroxyl oligomer was analyzed by Fourier transform infrared (FTIR). The oligomer sample was prepared on PTFE IR cards (Aldrich, Mississauga, ON. Canada) by casting from 1% w/v ADO oligomer in dichloromethane, followed by evaporation of the solvent under vacuum at room temperature. The oligomer-coated IR cards were stored in a dessicator until required for analysis. The IR spectra were recorded by means of an OMNIC E.S.P 5.20 version (Nicolet Instrument Corp., Thermo Nicolet, Madison, Wis.) in the transmission mode over a range of 600 cm$^{-1}$ to 4000 cm$^{-1}$. The IR transmission was obtained under a nitrogen gas purge using 120 scans averaged into one final spectrum. $^1$H NMR spectra were obtained on a Varian model HA-200 spectrometer using CDCl$_3$-d as the solvent.

Contact angle measurement: The surface polar character was used as indication of surface energy. PU materials with and without the addition of ADO were evaluated by measuring the receding contact angle formed between the sessile water droplet and the material surface using a goniometer system (Rame-hart, Model 100, Netcong, USA). 10% polymer solutions were prepared by dissolving PU alone or with 0.05, 0.5 and 5% (wt %) ADO in pyridine. The solutions were cast on clean glass cover slips and dried at room temperature overnight, followed by vacuum drying at room temperature for two days. Measurements were carried out with 0.5 μL distilled, deionized water drops, and ten measurements were done for each material.

Fabrication of fibrous porous scaffolds: PU alone and with different concentrations of ADO ranging from 0.05% to 5% (relative to the base polymer) were blended at 20 wt % in 1,1,1,3,3,3-hexafluoro-2-propanol (HFIP, Aldrich) and stirred at room temperature until they formed a clear solution. The polymer solution was fed by a syringe pump (PHD 2200, Harvard Apparatus) into an 18" stainless steel needle suspended vertically over a grounded aluminum collector plate. A high-voltage generator (Gamma High-Voltage Research) was employed with a 15 kV voltage to charge the steel needle containing the polymer solution [29]. The distance (15 cm) between the needle and collector, flow rate (0.5 ml/hr) of the polymer solution, and applied voltages (12 kv) were optimized to allow the formation and deposition of nano-scale fibrous scaffold up to 250 μm thick. Deposited scaffolds were allowed to dry under vacuum for a week at room temperature. The scaffolds were punched into 6-mm-diameter discs, and sterilized by γ irradiation at 4 Mred. The as-made fibrous scaffolds were sputter coated with gold and evaluated using Scanning Electron Microscopy (SEM, XL30 ESEM, FEI, Toronto, ON).

Annulus fibrosus cell culture on the porous scaffolds: Bovine caudal spines (6-9 months of age) were harvested aseptically and the AF dissected out. Five discs obtained from one caudal spine were combined to obtain sufficient cells for each experiment. Separate caudal spines were used for each set of experiments. The AF tissue was minced and underwent sequential enzymatic digestion with 0.5% protease (Sigma, St. Louis, Mo.) for 1 hour at 37° C., followed by 0.2% collagenase A (Roche, Laval, Quebec, Canada) overnight at 37° C. The cell suspension was washed, filtered through a sterile mesh, and resuspended in Ham's F12 supplemented with 5% fetal bovine serum (FBS). The cells ($5\times10^5$ cells/40 μl) were placed on scaffolds (8 mm diameter×250 μm thickness) in 96 well plates, which had been preconditioned for 3 hours in Ham's F12 medium at 37° C. The cells were allowed to adhere for 24 hours, and then the scaffolds were transferred to 24-well plates and grown in Ham's F12 supplemented with 20% FBS and cultured for various times up to 7 days. The medium was changed every 2 days. Each experiment was repeated at least 3 times and all conditions were done in triplicate.

Cell attachment: To evaluate cell attachment, an aliquot of cells ($5\times10^5$ cells/40 μl) was applied to the top surface of the scaffold and allowed to adhere for 2 hours, after which 250 μL of media was added. To determine the role of protein adsorption and scaffold chemistry on cell attachment, the cells were seeded serum-free in Ham's F12 in the presence or absence of cycloheximide (Sigma, St. Louis, Mo., 10 μg/mL final concentration). Cycloheximide was used to prevent protein synthesis. Cells seeded in the presence of this compound were pre-incubated for 4 hours with cyclohexamide before seeding. The cell-seeded scaffolds were harvested at 24 hours and cell attachment quantified by determining DNA content. To determine the percent cell attachment to the scaffold the DNA content of the cell-seeded scaffolds at 24 hours was divided by the DNA content of the cell aliquot used to seed the scaffold.

DNA content: To evaluate cellularity, samples were harvested at 24 hours and 7 days and papain digested (Sigma; 40 μg/mL, 20 mmol/L ammonium acetate, 1 mmol/L EDTA, and 2 mmol/L dithiothreitol) for 48 hours at 65° C. The DNA content of the cells was determined from aliquots of the papain digest using the Hoechst 33258 dye binding assay (Polysciences, Warrington, Pa.) and fluorometry (emission wavelength 365 nm, excitation wavelength 458 nm) as previously described [40]. A standard curve was generated using calf thymus DNA (Sigma).

AF cell morphology: To observe the morphology of AF cells 24 hours after seeding, the cell-scaffold constructs were rinsed in Ca$^{2+}$ and Mg$^{2+}$ free PBS three times, fixed in 2.5% gluteraldehyde for 1 hour, and then dehydrated in a series of ethanol (i.e. 50%, 70%, 90%, 100%) before critical point drying. All samples were sputter coated with gold and evaluated using scanning electron microscopy (SEM).

Proteoglycan and Collagen Quantification: The proteoglycan content was determined by quantifying the amount of sulfated glycosaminoglycans in the papain-digested tissue using the dimethylmethylene blue dye binding assay and spectrophotometry at 525 nm, as previously prescribed [40]. The standard curve was generated using bovine chondroitin sulfate (Sigma). To quantify collagen content, 100 μL aliquots of the papain digests were hydrolyzed in an equal volume of 6 N HCl for 18 hours at 110° C., neutralized using 5.7 N NaOH and diluted with distilled water. The hydroxyproline content was determined using the chloramine-T/Ehrlich's reagent assay and spectrophotometry (wavelength 560 nm) [41]. The standard curve was generated using L-hydroxyproline (Sigma). Collagen content was determined by assuming that hydroxyproline constitutes approximately 10% of the weight of collagen [41]. Data were normalized for cellularity. Cell-free scaffolds incubated in medium served as control.

Statistical analysis: Data from all experiments were combined and expressed as the mean±standard error of the mean. The data were analyzed using a one-way analysis of variance and all pair-wise comparisons between groups were conducted using the Scheffe post hoc test. Significance was assigned at p-values less than 0.05.

Results

Characterization of ADO: In one mole of ADO, 58.3±5.9% of the methylene side chains were hydrolyzed to carboxylic acid groups (—COOH). By retaining some hydrophobic character, the relative stability of the additive in the polymer can be controlled when the materials are incubated in aqueous medium. Increased hydrolysis of the lysine esters can be generated by prolonging the hydrolysis time [42].

Figure 9:
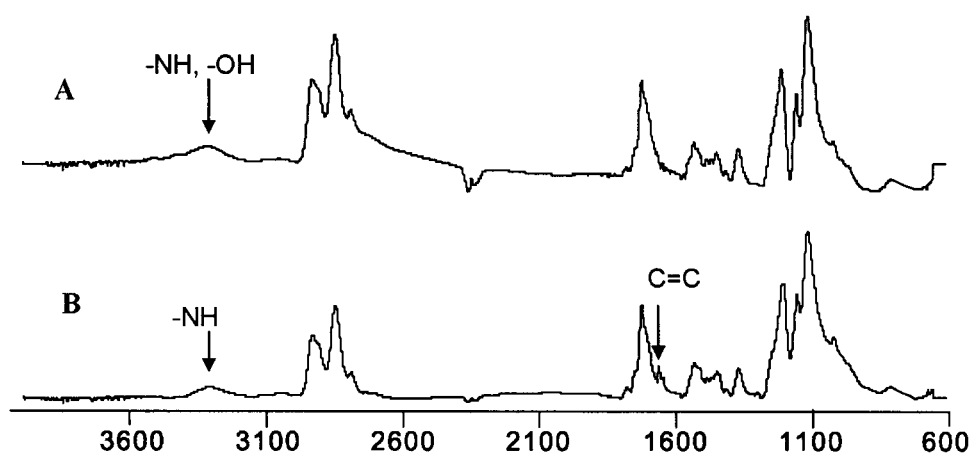
FIG. 9 is a FTIR spectra of the anionic dihydroxyl oligomer (ADO) (A), and the oligomer precursor (B).

The chemical groups of the synthesized ADO oligomer were examined using FTIR and compared with those of the oligomer before hydrolysis (FIG. 9). The spectra showed absorption bands in the 600 cm$^{-1}$-4000 cm$^{-1}$ region. A strong peak centered at 1735 cm$^{-1}$ was assigned to the urethane group in both oligomers [43]. The spectrum of ADO containing the carboxylic acid group was not significantly different from that of the oligomer containing ester groups in both backbone and side chains. This may be because the absorbance of the carbonyl group associated with the carboxylic acid overlapped with that of urethane groups. The ester groups linking vinyl groups on the two terminal ends were cleaved resulting in hydroxyl groups during the hydrolysis process since a peak at 1650 cm$^{-1}$ assigned to C=C bonds [44] (FIG. 9B) of the oligomer, prior to hydrolysis was eliminated, while the peak at 3335 cm$^{-1}$ corresponding to the secondary amine in the urethane linkages became broader due to the contribution of the hydroxyl group [45]. $^1$H NMR data also confirmed the cleavage of the vinyl groups by hydrolysis since two peaks corresponding to the C=C associated with HEMA at 5.50 ppm and 6.10 ppm [46] were no longer observed in the $^1$H NMR spectrum of the oliogomer (ADO) after hydrolysis (data not shown).

Figure 10:
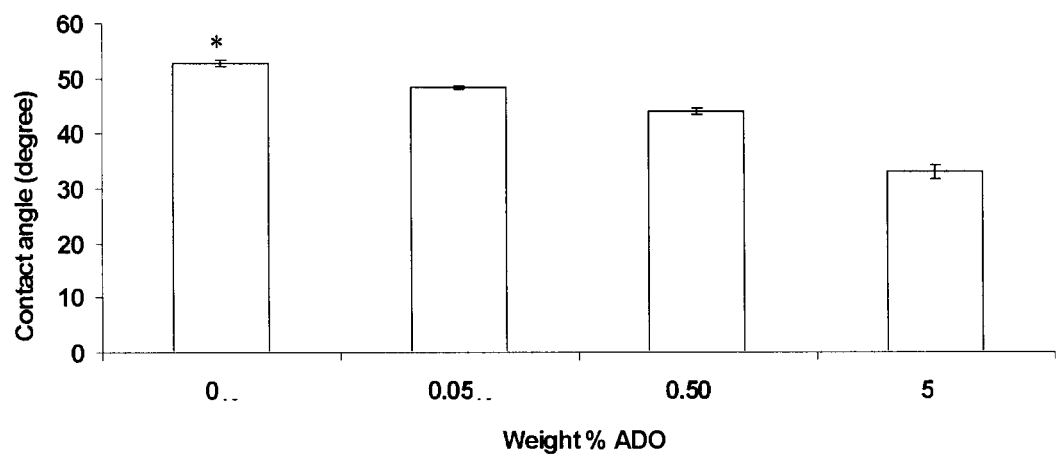
FIG. 10 is a graph showing water contact angle measurements of PU materials containing 0%, 0.05%, 0.5% and 5% ADO content (wt %). The results are reported as mean±standard error of the mean. * indicates significant difference from all other scaffolds (n=10).

Contact angle measurement: All PU materials containing the anionic dihydroxyl oligomer had significantly lower contact angles when compared to the PU polymer alone (FIG. 10). The contact angle value significantly decreased with an increase in ADO content indicating that the carboxylic acid and hydroxyl groups were present on the surface of these ADO-mixed PU materials. This was likely because of their relatively low molecular weight allowing them to migrate within the polymer matrix and their surfactant-like character, a relatively hydrophobic central portion and hydrophilic terminal segment with urethane, carboxylic acid and hydroxyl groups which contributed to the increased hydrophility of the surface.

Figure 11:
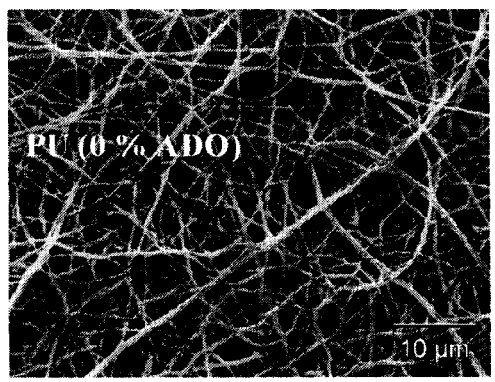
FIG. 11 shows SEM images of as-made PU scaffolds containing various amounts of ADO content (at 0%, 0.05%, 0.5% and 5% wt %).
Figure 11:
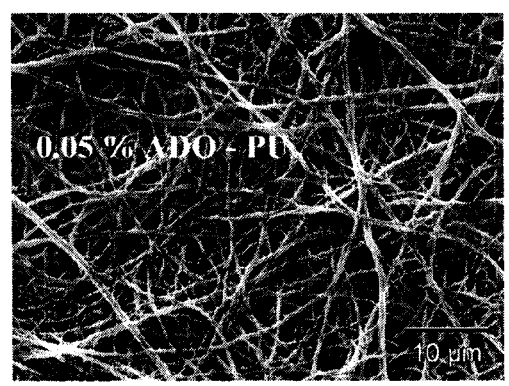
Figure 11:
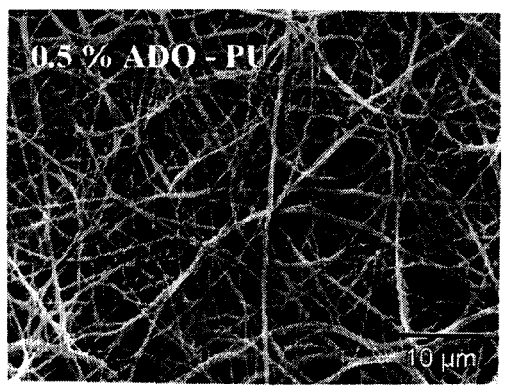
Figure 11:
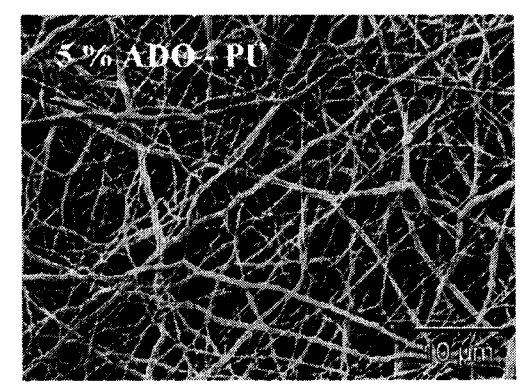

Appearance of fibrous porous scaffolds: As shown in FIG. 11, PU could be electrospun to form a porous fibrous scaffold. The fibers had an average thickness of 273 nm ranging from 130 to 890 nm. All scaffolds, independent of the amount of ADO, had a similar appearance with interconnected randomly distributed pores. The addition of ADO did not affect the size or orientation of the fibers. The pores formed between overlaying fibers appeared to be interconnected.

Cell attachment to scaffolds: Annulus fibrosus cells attached to the different PU scaffolds, however the percentage of cells that attached was influenced by the surface polarity. In the presence of serum the scaffolds containing ADO retained significantly more cells when compared to the PU scaffold without ADO as shown in FIG. 12A. The number of cells that attached increased with the addition of ADO up to 0.5 wt %, with no further increase seen in scaffolds containing 5 wt % ADO.

To determine if cell attachment was mediated by the adhesion of serum proteins, the percentage of cell attachment was determined in the absence of serum. As shown in FIG. 12B, cell attachment to scaffolds composed of PU alone or 0.05% ADO-containing PU scaffolds (lowest ADO concentration), was not affected by the absence of serum proteins. However, significantly fewer cells attached to PU scaffolds containing either 0.5% or 5% ADO in the absence of serum proteins. A further significant decrease in cell attachment to these two scaffolds was observed when protein synthesis by the cells was also inhibited following incubation with cycloheximide. The presence of cycloheximide did not significantly affect cell adhesion to scaffolds composed of either PU alone or PU containing 0.05% ADO. Cycloheximide did not appear to alter cell viability, as similar numbers of cells attached to PU only scaffolds in the presence or absence of this compound.

Morphology of AF cells attached to fibrous PU scaffolds: After 24 hours of adhesion, the morphology of AF cells adhering onto the fibrous scaffolds made of PU alone and PU containing various concentrations of ADO were evaluated using SEM. All cells were round and surface polarity in the ranges examined seemed to have no effect on AF cell shape in the first 24 hours as the cells on the different scaffolds all looked similar. (FIG. 13)

Figure 14:
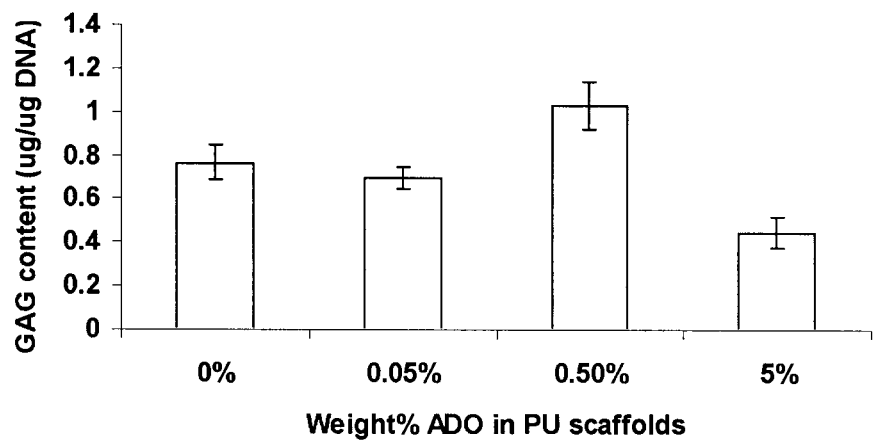
FIG. 14 are graphs showing extracellular matrix accumulation on PU scaffolds containing 0%, 0.05%, 0.5% and 5% ADO (wt %) after 7 days of culture. The glycosaminoglycan (GAG) content (A) and collagen content (B) were determined as described in the Examples. The data was pooled and expressed as mean±standard error of the mean. * indicates significant difference from scaffolds containing 0.05% or no ADO (n=9).
Figure 14:
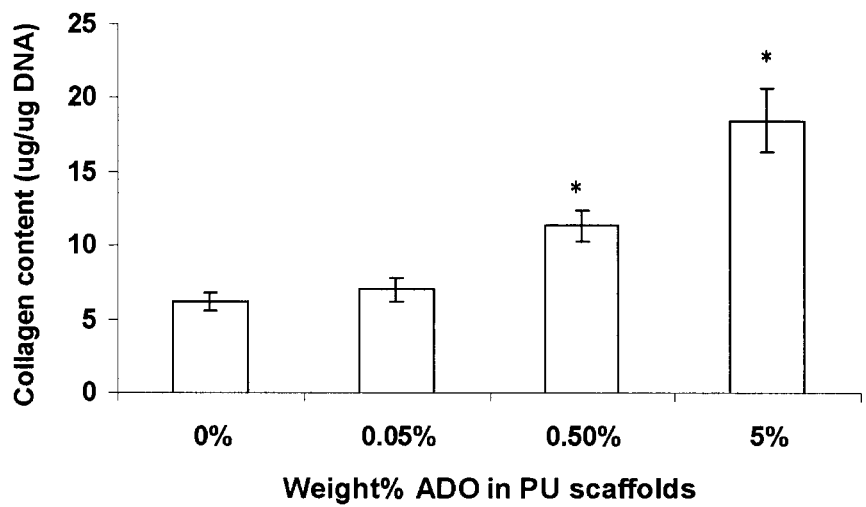

Matrix accumulation on PU scaffolds: To determine if cells grown on PU scaffolds can accumulate extracellular matrix, the amount of collagen and proteoglycans accumulated by 7 days of culture was quantified. These are the major components of AF tissue. Annulus fibrosus cells grown on all scaffolds produced and accumulated proteoglycans and collagen (FIG. 14). There was no significant difference in the amount of collagen accumulated by cells grown on scaffolds of PU alone or PU-0.05% ADO scaffolds. However cells grown on scaffolds containing higher concentrations of ADO content (0.5% and 5%) accumulated significantly more collagen when compared to the other scaffolds. Very small amounts of proteoglycans were accumulated by cells grown on all the scaffolds and there were no significant differences between the different scaffolds.

Discussion

Figure 12:
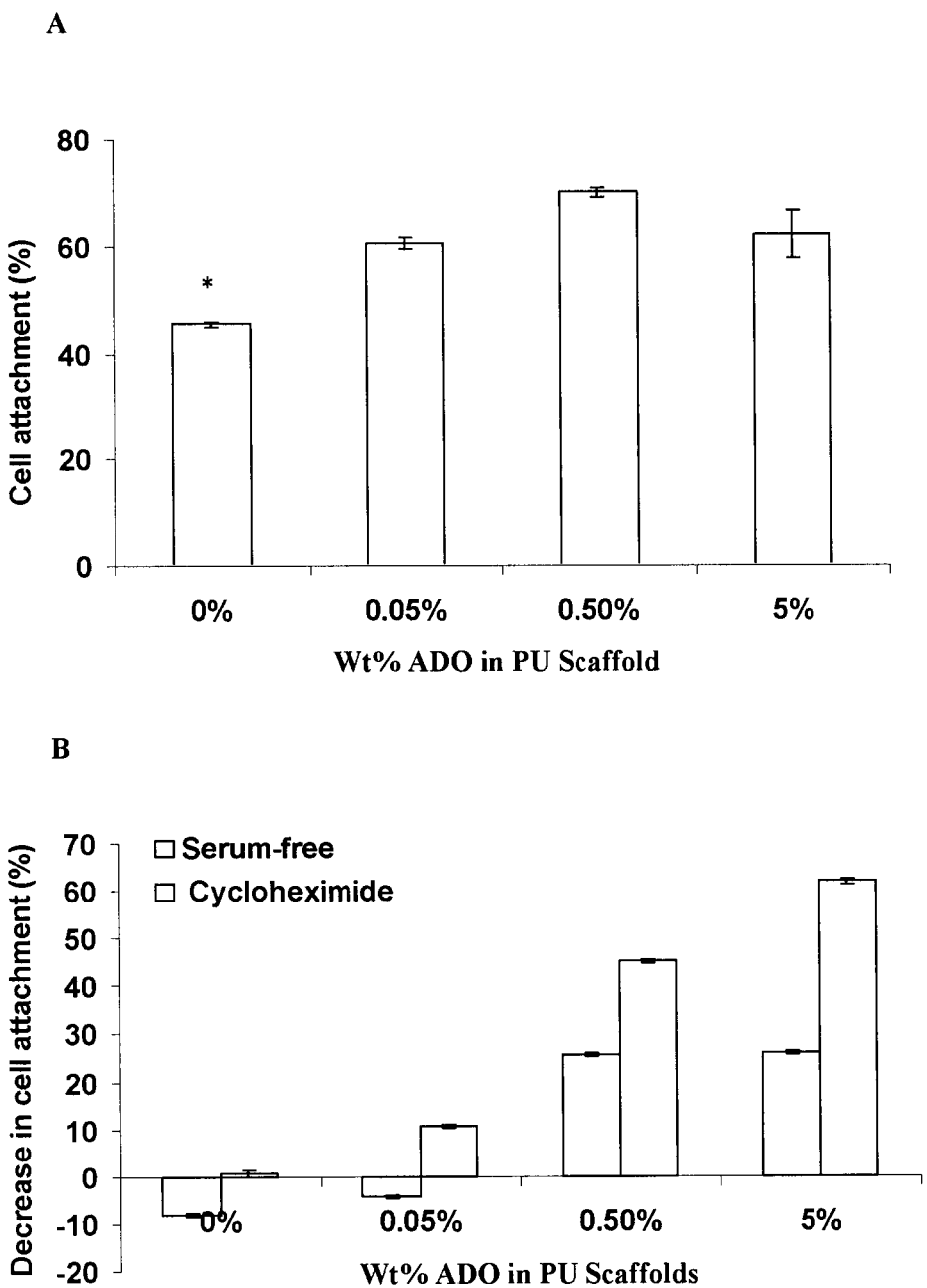
FIG. 12 are graphs showing: (A) Percent AF cell attachment 24 hours after seeding PU scaffolds formed in the presence of ADO (0.05%, 0.5% and 5% (wt %)) or absence of ADO in the presence of 5% fetal bovine serum. (B) AF cell attachment at 24 hours after seeding in serum-free DMEM in the absence or presence of cyclohexamide (10 μg/ml). The data are presented as a percent decrease in attachment and was calculated by dividing the % cell attachment for the test condition by the percent attachment in the presence of serum. The results from 3 different experiments were pooled and expressed as mean±standard error of the mean (n=9). * indicates significant difference, p<0.05.

This study demonstrated that biodegradable polyurethanes can be electrospun to form porous nano-fibrous scaffolds that support ECM accumulation by annulus fibrosus cells. Enhancing the surface energy by adding in different amounts of ADO with strong polar chemistry decreased the water contact angle (FIG. 10) and enhanced cell attachment (FIG. 12). However, the latter effect appeared to be associated with an optimal concentration of the ADO rather than simply increasing polar/hydrophilic character because when the contact angle decreased below 33° no further enhancement of cell attachment was seen. This could be related to electrorepulsion of the cells by the negatively charged (—COO$^-$) groups on the scaffold, as less cells appeared to attach to the scaffold (PU-5% ADO) with the highest surface energy (i.e. lowest contact angle) when compared to PU alone. Gao et al. showed that poly(glycolic acid) mesh after surface hydrolysis retained more than twice as many smooth muscle cells as compared to unmodified mesh, as a result of the transformation of ester groups on the mesh surface to carboxylic acid and hydroxyl groups, therefore both chemical functional groups contributing to the increased polar character [47]. Similarly AF cells showed greater attachment to PDLLA/Bioglass® composite foam scaffolds with increasing amounts of Bioglass, which was correlated with an increase in surface energy [48].

Surface polar chemistry affects AF cell attachment. At a lower ADO content (PU alone vs PU with 0.05% ADO) it appears that the surface chemistry alone is directly influencing cell adhesion since the presence or absence of serum has no influence on cell adhesion. However, at higher concentrations of ADO the increasing polar character (PU-0.5% ADO or PU-5% ADO) mediates its effect on cell attachment by influencing the adhesion of proteins from the serum and the newly synthesized protein by the cells as fewer cells attached in the absence of serum and even fewer cells adhered when protein synthesis by the cells was simultaneously inhibited (in presence of cycloheximide). Although in the latter condition, it is also possible that cyclohexamide may have altered the synthesis of cell surface adhesion molecules, thereby influencing the number of cells that attached. However, this is considered less likely as cell attachment was not affected by cyclohexamide when cells were seeded on PU or PU/0.05% ADO scaffolds.

Considering that various cell adhesion-promoting proteins (i.e. fibronectin,) exist in FBS [51], and can be produced by AF cells [52] it is possible that the enhanced surface energy, generated as a result of ionic (—COO$^-$) and hydrophilic (—OH) groups on the surface, altered the adsorption of specific adhesion protein(s) onto PU-ADO scaffolds (this is particularly a feature of PU-0.5% ADO) which yielded the highest number of adsorbed AF cells onto the scaffold.

It was interesting to note that the influence of the polar character remains even after a layer of protein has been adsorbed on the surface of the scaffolds. Cells grown on PU containing 0.5% and 5% ADO accumulated significantly more collagen when compared to cells cultured on scaffolds with lower or no ADO. Proteoglycans (as indicated by GAG content) were not similarly affected but since they are highly negatively charged, it is possible that these molecules were repelled from the surface. This would explain why the GAG content on PU-5% ADO scaffolds was the lowest. Interestingly, the ratio of collagen to GAG in the tissue formed by bovine AF cells grown for 7 days on fibrous scaffolds made of PU alone or PU containing 0.05%, 0.5% ADO content were 8.05, 10.01, and 10.96 respectively. Even though these values are only one third that of native bovine caudal AF tissue (native AF tissue 29.53±3.13 mean±SE, 6-9 month old calves), they are much higher than that reported for other tissue engineered in the literature (around 2) [31, 48].

In summary, nano-fibrous polyurethane scaffolds were successfully fabricated using electrospinning. The addition of an anionic dihydroxyl oligomer (ADO) to the polyurethane scaffolds increased the polar character as measured by a reduction in the water contact angle. Polar chemistry positively affected cell attachment. The increase was mediated by the level of ADO, either by the surface charge (at lower levels) and/or through its effects on protein(s) adsorption to the scaffold (at the higher levels). AF cells cultured on these scaffolds accumulated extracellular matrix and more collagen accumulated on scaffolds with higher ADO content. This indicates that surface energy influences AF cell attachment and collagen accumulation. The PU scaffold containing 0.5 wt % ADO may be the preferred formulation of the biomaterial for engineering annulus fibrosus tissue.

Having illustrated and described the principles of the invention in a preferred embodiment, it should be appreciated to those skilled in the art that the invention can be modified in arrangement and detail without departure from such principles. All modifications coming within the scope of the following claims are claimed.

All publications, patents and patent applications referred to herein are incorporated by reference in their entirety to the same extent as if each individual publication, patent or patent application was specifically and individually indicated to be incorporated by reference in its entirety.

LIST OF PUBLICATIONS

1. Miller J A, Schmatz B S, Schultz A B. Lumbar disc degeneration: correlation with age, sex, and spine level in 600 autopsy specimens. Spine 1988; 13:173-78.
2. Grunhagen T, Wilde G, Soukane D M, Shirazi-Adl S A, Urban J P. Nutrient supply and intervertebral disc metabolism. J Bone Joint Surg Am. 2006; 88: Suppl 2:30-5. Review.
3. Ferguson S J, Steffen T. Biomechanics of the aging spine. Eur Spine J, 2003; 12 Suppl 2: S97-S103.
4. Yoganandan N, Larson S J, Pintar F A, Gallagher M, Reinartz J, Droese K. Intravertebral pressure changes caused by spinal microtrauma. Neurosurgery. 1994; 35: 415-21; discussion 421.
5. Antonacci M D, Mody D R, Rutz K, Weilbaecher D, Heggeness M H. A histologic study of fractured human vertebral bodies. J Spinal Disord Tech. 2002; 15:118-26.
6. Batti C, Videman T. Lumbar disc degeneration: epidemiology and genetics. J Bone Joint Surg Am. 2006; 88: Suppl 2:3-9.
7. Merkesdal S, Mau Wilfried. Prediction of costs-of-illness in patients with low back pain undergoing orthopedic outpatient rehabilitation. International J Rehab Res 2005; 28: 119-126.
8. Humphreys, S. C, Eck, J, Hodges, S. D. Neuroimaging in Low Back Pain. Am Fam Physician 2002; 65: 2299-306.
9. Lopez-Espina C G, Amirouche F, Havalad V. Multilevel cervical fusion and its effect on disc degeneration and osteophyte formation. Spine 2006; 31: 972-978.
10. Shim C S, Lee S H, Shin H D, Kang H S, Choi W C, Jung B et al. CHARITE versus ProDisc: a comparative study of a minimum 3-year follow-up. Spine 2007; 32:1012-1018.
11. Zigler J, Delamarter R, Spivak J M, Linovitz R J, Danielson G O, III, Haider T T et al. Results of the prospective, randomized, multicenter Food and Drug Administration investigational device exemption study of the Propisc-L total disc replacement versus circumferential fusion for the treatment of 1-level degenerative disc disease. Spine 2007; 32:1155-1162.
12. Anderson P A, Rouleau J P. Intervertebral disc arthroplasty. Spine 2004; 29: 2779-86.
13. Lotz J C, Kim A J. Disc regeneration: why, when, and how. Neurosurg Clin N Am. 2005; 16: 657-663, vii. Review.
14. Alini M, Li W, Markovic P, et al. The potential and limitations of a cell-seeded collagen/hyaluronan scaffold to engineer an intervertebral disc-like matrix. Spine 2003; 28: 446-54.
15. Yang S H, Chen P Q, Chen Y F, Lin F H. An in-vitro study on regeneration of human nucleus pulposus by using gelatin/chondroitin-6-sulfate/hyaluronan tri-copolymer scaffold. Artif Organs. 2005; 29: 806-14.
16. Yang S H, Chen P Q, Chen Y F, Lin F H. Gelatin/chondroitin-6-sulfate copolymer scaffold for culturing human nucleus pulposus cells in vitro with production of extracellular matrix. J Biomed Mater Res B Appl Biomater. 2005; 74: 488-94.
17. Hamilton D J, Seguin C A, Wang J, Pilliar R M, Kandel R A. Formation of a nucleus pulposus-cartilage endplate construct in vitro. Biomaterials. 2006; 27:397-405.
18. Bogduk N. The inter-body joints and the intervertebral discs. In: Bogduk N, ed. Clinical Anatomy of the Lumbar Spine and Sacrum. New York: Churchill Livingstone, 1997:13-31.
19. Helen W, Gough J E. In vitro studies of annulus fibrosus disc cell attachment, differentiation and matrix production on PDLLA/45S5 Bioglass composite films. Biomaterials 2006; 27: 5220-5229.
20. Sato M, Kikuchi M, Ishihara M, Asazuma T, Kikuchi T, Masuoka K, et al. An atelocollagen honey-comb-shaped scaffold with a membrane seal (ACHMS-scaffold) for the culture of annulus fibrosus cells from an intervertebral disc. J Biomed Mater Res 2003; 64(A): 249-56.
21. Rong Y, Sugumaran G, Silbert J E, Spector M. Proteoglycans synthesized by canine intervertebral disc cells grown in a type I collagen—glycosaminoglycan matrix. Tissue Eng 2002; 8:1037-47.
22. Alini M, Li W, Markovic P, Aebi M, Spiro R C, Roughley P J. The potential and limitations of a cell-seeded collagen/hyaluronan scaffold to engineer an intervertebral disc-like matrix. Spine 2003; 28: 446-54.
23. Mizuno H, Roy A, Vacanti C A, Kojima K, Ueda M, Bonassar L J. Tissue-engineered composites of annulus fibrosus and nucleus pulposus for intervertebral disc replacement. Spine 2004; 29: 1290-1298.
24. Thonar E, An H, Masuda K. Compartmentalization of the matrix formed by nucleus pulposus and annulus fibrosus cells in alginate gel. Biochem Soc Trans 2002; 30: 874-8.
25. Li H Y, Chang J. pH-compensation effect of bioactive inorganic fillers on the degradation of PLGA. Comp Sci Tech 2005; 65: 2226-2232.
26. Ishihara H, Urban J P. Effects of low oxygen concentrations and metabolic inhibitors on proteoglycan and protein synthesis rates in the intervertebral disc. J Orthop Res 1999; 17: 829-835.
27. Stankus J, Guan J J, Fujimoto K, Wagner W R. Microintegrating smooth muscle cells into a biodegradable, elastomeric fiber matrix. Biomaterials 2006; 27: 735-744.
28. Riboldi S, Sampaolesi M, Neuenschwander P, Cossu G, Mantero S. Electrospun degradable polyesterurethane membranes: Potential scaffolds for skeletal muscle tissue engineering. Biomaterials 2005; 26: 4606-4615.
29. Stankus J J, Guan J J, Wagner W R. Fabrication of biodegradable elastomeric scaffolds with sub-micron morphologies. J Biomed Mater Res 2004; 70A: 603-614.
30. Zhong S, Teo W E, Zhu X, Beuerman R, Ramakrishna S, Yung L Y L. Formation of collagen-glycosaminoglycan blended nanofibrous scaffolds and their biological properties. Biomacromolecules 2005; 6: 2998-3004.
31. Thapa A, Webster T J, Haberstroh K M. Nano-structured polymers enhance bladder smooth muscle cell function. Biomaterials 2003; 24: 2915-2926.
32. Nerurkar N L, Elliott D M, Mauck R L. Mechanics of oriented electrospun nanofibrous scaffolds for annulus fibrosus tissue engineering. J Orthop Res. 2007; 25:1018-28.
33. Hallab N, Bundy K, O'Connor K, Moses R L, Jacobs J J. Evaluation of metallic and polymeric biomaterial surface energy and surface roughness characteristics for directed cell adhesion, Tissue Eng. 2001; 71: 55-71.
34. Satriano C, Carnazza S, Guglielmino S, Marietta G. Surface free energy and cell attachment onto ion-beam irradiated polymer surfaces. Nuclear Instruments and Methods in Physics Research 2003; B 208: 287-293.
35. Yamamoto A, Mishima S, Maruyama N, Sumital M. Quantitative evaluation of cell attachment to glass, polystyrene, and fibronectin- or collagen-coated polystyrene by measurement of cell adhesive shear force and cell detachment energy. J Biomed Mater Res 2000; 50: 114-124.
36. Lin Y, Wang L, Zhang P, Wang X, Chen X, Jing X, Su Z. Surface modification of poly(L-lactic acid) to improve its cytocompatibility via assembly of poly electrolytes and gelatin. Acta Biomaterialia 2006; 2: 155-164.
37. Schneider G B, English A, Abraham M, Zaharias R, Stanford C, Keller J. The effect of hydrogel charge density on cell attachment. Biomaterials 2004; 25: 3023-3028.
38. Choee M I, Lee S J, Lee S J, Lee Y M, Rhess J M, Lee H B, Khang G. Proliferation Rate of Fibroblast Cells on Polyethylene Surfaces with Wettability Gradient. J Appl Polym Sci 2004; 92: 599-606.
39. Tang Y W, Labow R S, Santerre J P. Enzyme-induced biodegradation of poly carbonate polyurethanes: Dependence on hard-segment concentration. J Biomed Mater Res 2001; 56: 516-528.
40. Waldman S D, Grynpas M, Pilliar R M, Kandel R A. Characterization of cartilaginous tissue formed on calcium polyphosphate substrates in vitro. J Biomed Mater Res 2002; 62: 323-330.
41. Woessner J F, Jr. The determination of hydroxyproline in tissue and protein samples containing small proportions of this imino acid. Arch Biochem Biophys 1961; 93: 440-447.
42. Emsting M, Bonin G, Yang M L, Labow R S. Santerre J P. Generation of cell adhesion substrates using peptide fluoroalkyl surface modifiers. Biomaterials 2005; 20: 6536-6546.
43. Shin B C, Myung S W, Tang S, Zhang Y, Kim Y S, Choi H S. Plasma-induced graft co-polymerization of acrylic acid onto the polyurethane surface. Surface and Coatings Technology 2004; 182: 55-64.
44. Yang L, Wang J, Hong J, Santerre, J P, Pilliar R M. Synthesis and characterization of a novel polymer-ceramic system for biodegradable composite application. J Biomed Mater Res. 2003; 66A: 622-632
45. Guan J J, Gao C Y, Feng L X, Shen J C. Functionalizing of polyurethane surfaces by photografting with hydrophilic monomers. J Appl Polym Sci 2000; 77: 2505-2512.
46. Atta A M, Elnagdy S I, Abdel-Raouf M E, Elsaeed S M, Abdel A A. Compressive Properties and Curing Behaviour of Unsaturated Polyester Resins in the Presence of Vinyl Ester Resins Derived from Recycled Poly(ethylene terephthalate). J Poly Res 2005; 12: 373-383.
47. Michiardi A, Aparicio C, Ratner B D, Planell J A, Gil J. The influence of surface energy on competitive protein adsorption on oxidized NiTi surfaces. Biomaterials 2007; 28: 586-594.
48. Gao J, Niklason L, Langer R. Surface hydrolysis of poly (glycolic acid) meshes increases the seeding density of vascular smooth muscle cells. J Biomed Mater Res. 1998; 42: 417-24.
49. Helen W, Merry C L R, Blaker J J, Gough J E. Three-dimensional culture of annulus fibrosus cells within PDLLA/Bioglass® composite foam scaffolds: Assessment of cell attachment, proliferation and extrcellular matrix production. Biomaterials 2007; 28: 2010-2020.
50. Fang F, Satulovsky J, Szleifer I. Kinetics of protein adsorption and desorption on surfaces with grafted polymers. Biophysical J. 2005; 89: 1516-1533.
51. Hayman E G, Pierschbacher M D, Suzuki S, Ruoslahti E. Vitronectin—a major cell attachment—promoting protein in fetal bovine serum. Exp Cell Res. 1985; 160: 245-258.
52. Hayes A J, Benjamin M, Ralphs J R. Extracellular matrix in development of the intervertebral disc. Matrix Biol. 2001; 20: 107-21.
53. Chang G, Kim H J, Kaplan D, Vunjak-Novakovic G, Kandel R A. Annulus fibrosus tissue grown on porous silk scaffolds. Eur Spine J, 2007, Apr. 20, Epub.
54. Meinel L, Hofmann S, Karageorgiou V, Zichner L, Langer R, Kaplan D, Vunjak-Novakovic G. Engineering cartilage-like tissue using human mesenchymal stem cells and silk protein scaffolds. Biotechnol Bioeng. 2004; 88: 379-91.
55. Zhu H, Mitsuhashi N, Klein a, Barshy L W, Weinberg K, Barr M L, Demetriou A, Wu G D. The role of the hyaluronan receptor CD44 in mesenchymal stem cell migration in the extracellular matrix. Stem Cells. 2006; 24:928-35.
56. Stevens J W, Kurriger G L, Carter A S, Maynard J A. CD44 expression in the developing and growing rat intervertebral disc. Dev Dyn 2000; 219: 381-390.
57. Kogerman P, Sy M S, Culp L A. CD44 protein levels and its biological activity are regulated in Bal b/c 3T3 fibrobalsts by serum factors and by transformation with the ras but not with the sis oncogene. J Cell Physiol. 1996; 169: 341-349.
58. Redey S A, Nardin M, Bemache-Assolant D, Rey C, Delannoy P, Sedel L, Marie P J. Behavior of human osteoblastic cells on stoichiometric hydroxyapatite and type A carbonate apatite: Role of surface energy. J Biomed Mater Res 2000; 50: 353-364.

What is claimed is:

1. A fibrous scaffold for culturing soft tissues on its surface, said scaffold comprising fibres comprising a blend of biodegradable polyurethane polymers and anionic dihydroxyl oligomers, wherein the concentration of the oligomers in the blend is less than about 5 wt % and the anionic dihydroxyl oligomers are characterized by one or both of the following properties:
   a) absorption bands in the about 600 $cm^{-1}$ to about 4000 $cm^{-1}$ region by Fourier transform infrared spectroscopy (FTIR); or
   b) a peak corresponding to a urethane group at about 1680 to about 1750 $cm^{-1}$, by FTIR.

2. A fibrous scaffold according to claim 1, wherein the fibres are random.

3. A fibrous scaffold according to claim 1, wherein the fibres are aligned.

4. A fibrous scaffold according to claim 1, which is a nanofiber porous scaffold.

5. A fibrous scaffold according to claim 1, wherein the biodegradable polyurethane polymers comprise hydrolysable polyurethane chains.

6. A fibrous scaffold according to claim 1, wherein the biodegradable polyurethane polymers are polycarbonate urethane polymers.

7. A fibrous scaffold according to claim 1 having a fibre thickness of between about 130 to about 1500 nm.

8. A process for preparing a fibrous scaffold as claimed in claim 1, comprising
   blending the biodegradable polyurethane polymers and anionic dihydroxyl oligomers to form a biodegradable polyurethane formulation, wherein the concentration of the oligomers in the formulation is less than about 5 wt %; and
   electrospinning the formulation to form the fibrous scaffold.

9. An engineered biological material characterized by a continuous layer of annulus fibrosus tissue on a fibrous scaffold according to claim 1.

10. A process for producing an engineered biological material of claim 9 comprising:
    (a) forming a layer of isolated annulus fibrosus cells on a fibrous scaffold for culturing soft tissues on its surface, said scaffold comprising fibres comprising a blend of biodegradable polyurethane polymers and anionic dihydroxyl oligomers; and
    (b) culturing the annulus fibrosus cells in culture media so that the annulus fibrosus cells accumulate extracellular matrix and form a continuous layer of annulus fibrosus tissue.

11. A method of replacing or repairing damaged, degenerated or deficient intervertebral discs or portions thereof of a patient, said method comprising implanting an engineered biological material according to claim 9 or annulus fibrosus tissue therefrom into the site of the damaged, degenerated or deficient intervertebral disc or portions thereof, of the patient.

12. A fibrous scaffold according to claim 1, wherein said biodegradable polyurethane polymers comprise lysine diisocyanate groups.

13. A fibrous scaffold according to claim 1, wherein said biodegradable polyurethane polymers are polyester urethane polymers.

14. A fibrous scaffold according to claim 1, wherein the concentration of the oligomers in the blend is less than about 0.5 wt %.

15. A fibrous scaffold according to claim 1, wherein said soft tissues are grown on the surface of said fibrous scaffold.

16. A fibrous scaffold for culturing soft tissues on its surface, said scaffold comprising fibres comprising a blend of biodegradable polyurethane polymers and anionic dihydroxyl oligomers, wherein the concentration of the oligomers in the blend is less than about 5 wt % and about 50% to about 70% of the anionic groups of said anionic dihydroxyl oligomers comprise carboxylic acid groups.

17. A fibrous scaffold according to claim 16, wherein the fibres are random.

18. A fibrous scaffold according to claim 16, wherein the fibres are aligned.

19. A fibrous scaffold according to claim 16, which is a nanofiber porous scaffold.

20. A fibrous scaffold according to claim 16, wherein the biodegradable polyurethane polymers comprise hydrolysable polyurethane chains.

21. A fibrous scaffold according to claim 16, wherein the biodegradable polyurethane polymers are polycarbonate urethane polymers.

22. A fibrous scaffold according to claim 16 having a fibre thickness of between about 130 to about 1500 nm.

23. A process for preparing a fibrous scaffold as claimed in claim 16, comprising
    blending the biodegradable polyurethane polymers and anionic dihydroxyl oligomers to form a biodegradable polyurethane formulation, wherein the concentration of the oligomers in the formulation is less than about 5 wt %; and
    electrospinning the formulation to form the fibrous scaffold.

24. An engineered biological material characterized by a continuous layer of annulus fibrosus tissue on a fibrous scaffold according to claim 16.

25. A process for producing an engineered biological material of claim 24 comprising:
    (a) forming a layer of isolated annulus fibrosus cells on a fibrous scaffold for culturing soft tissues on its surface, said scaffold comprising fibres comprising a blend of biodegradable polyurethane polymers and anionic dihydroxyl oligomers; and
    (b) culturing the annulus fibrosus cells in culture media so that the annulus fibrosus cells accumulate extracellular matrix and form a continuous layer of annulus fibrosus tissue.

26. A method of replacing or repairing damaged, degenerated or deficient intervertebral discs or portions thereof of a patient, said method comprising implanting an engineered biological material according to claim 24 or annulus fibrosus tissue therefrom into the site of the damaged, degenerated or deficient intervertebral disc or portions thereof, of the patient.

27. A fibrous scaffold according to claim 16, wherein said biodegradable polyurethane polymers comprise lysine diisocyanate groups.

28. A fibrous scaffold according to claim 16, wherein said biodegradable polyurethane polymers are polyester urethane polymers.

29. A fibrous scaffold according to claim 16, wherein the concentration of the oligomers in the blend is less than about 0.5 wt %.

30. A fibrous scaffold according to claim 16, wherein said soft tissues are grown on the surface of said fibrous scaffold.

* * * * *